United States Patent [19]

Andersen et al.

[11] Patent Number: 5,789,404
[45] Date of Patent: Aug. 4, 1998

[54] 3-SUBSTITUTED 1-ARYLINDOLE COMPOUNDS

[75] Inventors: Kim Andersen, Rodovre; Jens Kristian Perregaard, Jaegerspris, both of Denmark

[73] Assignee: H. Lundbeck A/S, Copenhagen-Valby, Denmark

[21] Appl. No.: 666,380

[22] PCT Filed: Dec. 15, 1994

[86] PCT No.: PCT/DK94/00470

§ 371 Date: Aug. 12, 1996

§ 102(e) Date: Aug. 12, 1996

[87] PCT Pub. No.: WO95/16684

PCT Pub. Date: Jun. 22, 1995

[30] Foreign Application Priority Data

Dec. 16, 1993 [DK] Denmark .................. 1395/93

[51] Int. Cl.$^6$ .............. C07D 403/12; C07D 209/14; C07D 209/10; A61K 31/40
[52] U.S. Cl. .................. 514/226.8; 514/228.2; 514/228.8; 514/235.2; 514/274; 514/315; 514/369; 514/376; 514/392; 514/415; 514/418; 544/54; 544/97; 544/59; 544/159; 544/158; 544/162; 544/163; 544/316; 546/201; 546/242; 546/243; 546/245; 546/277.4; 546/277.7; 546/246
[58] Field of Search .................. 548/186, 189, 548/229, 225, 312, 484, 485, 486, 490, 496, 491, 503, 504, 505; 544/54, 97, 59, 162; 546/201, 242, 243, 245, 246, 277.7, 277.4; 514/226.8, 228.2, 228.8, 235.2, 274, 369, 392, 415, 418, 315, 376

[56] References Cited

U.S. PATENT DOCUMENTS

| | | | |
|---|---|---|---|
| 3,720,771 | 3/1973 | Canas-Rodriguez et al. | 424/274 |
| 3,953,442 | 4/1976 | Demarne | 260/247.5 FP |
| 4,558,048 | 12/1985 | Bass | 514/232 |
| 5,216,001 | 6/1993 | Perregaard et al. | 514/323 |
| 5,317,025 | 5/1994 | Bru-Magniez et al. | 514/323 |
| 5,348,968 | 9/1994 | Lavielle et al. | 514/360 |
| 5,439,922 | 8/1995 | Perregaard et al. | 514/323 |
| 5,462,948 | 10/1995 | Perregaard et al. | 514/323 |
| 5,504,101 | 4/1996 | Glennon | 514/415 |

FOREIGN PATENT DOCUMENTS

| | | |
|---|---|---|
| 2242091 | 3/1975 | France |
| 1911893 | 9/1970 | Germany |

OTHER PUBLICATIONS

Khan et al., Arylindoles. III (1). Mannich Reaction of 1-Arylindoles, J. Heterocyclic Chem., 16(7), pp. 1483–1484, 1979.

Fauran et al., Chemical Abstracts, vol. 83, 163991b, 1975.

Canas–Rodriguez et al., Chemical Abstracts, vol. 75, 5690h, 1971.

Grinev et al., Chemical Abstracts, vol. 69, 86753g, 1968.

Primary Examiner—Mukund J. Shah
Assistant Examiner—Deepak R. Rao
Attorney, Agent, or Firm—Darby & Darby

[57] ABSTRACT

3-Substituted 1-arylindole compounds are provided having general formula (I)

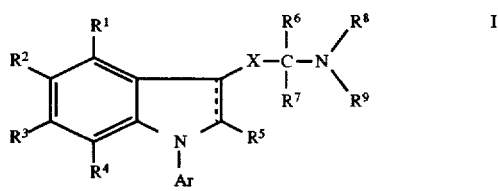

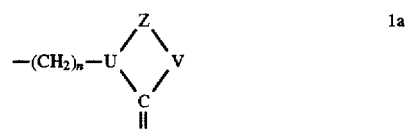

or

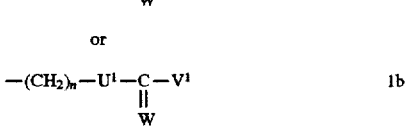

wherein Ar is an optionally substituted aryl group; X represents a divalent hydrocarbon group, methyleneoxy or -thioxo; $R^1$–$R^4$ are hydrogen or other substituents; $R^5$ is hydrogen, alkyl, alkenyl, etc.; $R^6$ and $R^7$ are independently hydrogen, alkyl, alkenyl, etc.; $R^8$ is alkyl, alkenyl or $R^8$ represents a group of formula 1a or 1b; wherein n is an integer from 2–8; W is O or S; U is N or CH; Z is $(CH_2)_m$, m being 2 or 3, 1,2-phenylene optionally substituted with halogen or trifluoromethyl, CH=CH, COCH$_2$ or CSCH$_2$; V is O, S, CH$_2$ or NR$^{10}$, wherein R$^{10}$ is hydrogen, alkyl, alkenyl, cycloalkyl, etc.; $U^1$ is O, S, CH$_2$ or a group NR$^{11}$, wherein R$^{11}$ is hydrogen, alkyl, alkenyl, etc.; and $V^1$ is NR$^{12}$R$^{13}$, OR$^{14}$, SR$^{15}$ or CR$^{16}$R$^{17}$R$^{18}$, where R$^{12}$–R$^{18}$ are as the R$^{10}$ substituents; R$^9$ is hydrogen, alkyl, alkenyl or alkynyl; or R$^9$ is linked to R$^7$ to form a ring; or R$^8$ and R$^9$ together with the nitrogen atom to which they are attached form a morpholinyl or piperidinyl ring, the latter optionally substituted by alky or a group of formula 1a or 1b, or a carbamoyl group. Said compounds show central antiserotonergic activity and are useful in the treatment of central nervous system disorders.

22 Claims, No Drawings

3-SUBSTITUTED 1-ARYLINDOLE COMPOUNDS

This application is a national stage application under 35 U.S.C. §371 claiming priority of PCT International Application No. PCT/DK94/00470, filed 15 Dec. 1994.

FIELD OF THE INVENTION

The present invention relates to novel 3-substituted 1-arylindole compounds and their acid addition salts, to methods for preparing such compounds, pharmaceutical compositions comprising the compounds as an active ingredient and to their use. The novel compounds show central antiserotonergic activity and possibly also antidopaminergic activity and are, accordingly, useful in the treatment of central nervous system (CNS) disorders.

BACKGROUND OF THE INVENTION

It is well known that serotonin (5-HT) receptor antagonists, in particular 5-HT$_2$ receptor antagonists, are useful in the treatment of CNS disorders. So, 5-HT$_2$ receptor antagonists have been reported to show effects in the treatment of anxiety, agression, depression, sleep disturbances, migraine, negative symptoms of schizophrenia, extrapyramidal side effects induced by conventional antipsychotics, abuse of drugs and substances of abuse and Parkinson's disease. For example reference may be made to the following:

The selective 5-HT$_2$ receptor antagonist ritanserin has been shown to be an antidepressant and to improve depressive symptoms of schizophrenia (E. Klieser, W. H. Strauss; Pharmacopsychiat. 21 (1988), pp. 391–393) and it has been demonstrated to exert effects in an animal test indicative of anxiolytic drug activity (F. C. Colpart et al.; Psychopharmacology (1985) 86; 303–305). Furthermore, ritanserin has been shown to improve the quality of sleep (P. A. J. Janssen; Pharmacopsychiat. 21 (1988), 33–37).

It is generally believed that 5-HT is involved in migraine attacks. The links between 5-HT and migraine attacks are several and they suggest a number of mechanisms whereby 5-HT may be involved (Scrip Report; "Migraine—Current trends in research and treatment"; PJB Publications Ltd.; May 1991).

Studies of the mixed serotonin and dopamine receptor antagonist setoperone indicate that blockade of 5-HT$_2$ receptors may be related to improvement of negative symptoms of schizophrenia (Ceulemans et al., Psychopharmacology (1985) 85, 329–332).

Finally, ritanserin has been found to relieve neuroleptic-induced parkinsonism (Bersani et al.; Clinical Neuropharmacology, 13, No. 6 (1990), 500–506) and to reduce abuse of alcohol and drugs (Meert et al., Pharmacopsychiatry, 24 (5), 1991, 159–163).

Damping of dopamine (DA) overactivity by the use of DA receptor blocking drugs is today the most important principle in the treatment of schizophrenia, in particular the positive symptoms thereof. "Classical neuroleptics" such as haloperidol, cis-(Z)-flupentixol and chlorpromazine are believed to induce antipsychotic effect via DA receptor blockade.

U.S. Pat. No. 4,710,500, corresponding to European Patent No. 0200322, discloses a class of optionally 5-substituted 1-aryl-3-piperidinyl, 1-aryl-3-(1,2,3,6-tetrahydropyridinyl)- or 1-aryl-3-piperazinylindole derivatives having potent 5-HT$_2$ antagonistic activity, and many of them additionally having potent dopamine D$_2$-antagonistic activity in vivo.

European Patent Application No.916010055.5 published as EP-A2-0465398 discloses a class of 6-substituted and/or 2-alkyl substituted indole and 2,3-dihydroindole derivatives having antiserotonergic activity.

It is the object of the present invention to provide new compounds having antiserotonergic, in particular 5-HT$_2$ antagonistic activity, and possibly also antidopaminergic activity.

SUMMARY OF THE INVENTION

It has now been found that compounds of a novel class of 3-substituted 1-arylindole compounds possess central antiserotonergic activity and some of them additionally antidopaminergic activity.

Accordingly, the present invention relates to novel compounds of general Formula I

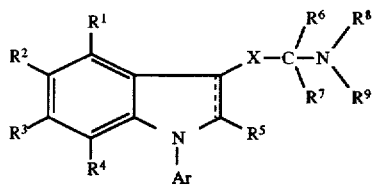

wherein Ar is selected from the group consisting of phenyl, 2-thienyl, 3-thienyl, 2-furyl, 3-furyl, 2-pyridyl, 3-pyridyl, and 4-pyridyl, and such groups substituted with one or more substituents selected from halogen, lower alkyl, lower alkoxy, hydroxy, trifluoromethyl, and cyano;

X represents a bond or a divalent spacer selected from the group consisting of A—CR$^a$R$^b$ and CR$^c$R$^d$, wherein A is O, S or CR$^e$R$^f$, and R$^a$ to R$^f$ are hydrogen, lower alkyl or lower alkenyl;

the dotted line designates an optional bond;

R$^1$-R$^4$ are independently selected from the group consisting of hydrogen, halogen, lower alkyl, lower alkoxy, hydroxy, nitro, lower alkylthio, lower alkylsulfonyl, lower alkyl- or dialkylamino, cyano, trifluoromethyl, trifluoromethylsulfonyloxy and trifluoromethylthio;

R$^5$ is hydrogen, hydroxy, lower alkoxy, halogen, trifluoromethyl, lower alkyl optionally substituted with hydroxy or lower alkenyl optionally substituted with hydroxy;

R$^6$ and R$^7$ independently represent hydrogen, lower alkyl or lower alkenyl;

R$^8$ is lower alkyl, lower alkenyl or lower alkyl or lower alkenyl substituted with one or two hydroxy groups, or R$^8$ represents a group of Formula 1a or 1b:

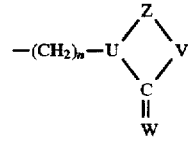

or

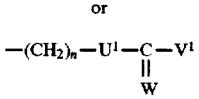

wherein n is an integer from 2–8; W is O or S; U is N or CH; Z is (CH$_2$)$_m$, m being 2 or 3, 1,2-phenylene optionally substituted with halogen or trifluoromethyl, CH=CH, COCH$_2$ or CSCH2—;

V is O, S, CH$_2$, or NR$^{10}$, wherein R$^{10}$ is hydrogen or lower alkyl, lower alkenyl, cycloalkyl or cycloalkyl-lower alkyl, each optionally substituted with one or two hydroxy groups;

U$^1$ is O, S, CH$_2$ or a group NR$^{11}$, wherein R$^{11}$ is selected among the R$^{10}$-substituents; and V$^1$ is NR$^{12}$R$^{13}$, OR$^{14}$, SR$^{15}$ or CR$^{16}$R$^{17}$R$^{18}$, where each of R$^{12}$-R$^{18}$ may be independently selected among the R$^{10}$-substituents;

R$^9$ is hydrogen, lower alkyl, lower alkenyl or lower alkynyl; or R$^9$ is linked to R$^7$ in order to form a 5–6 membered ring containing one nitrogen atom; or R$^8$ and R$^9$ together with the nitrogen atom to which they are attached form a group of Formula 1c

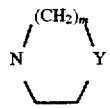

1c.

wherein m is 1 or 2, Y is O, S or a group CH—R$^{19}$ where R$^{19}$ is hydrogen, or lower alkyl or lower alkenyl, optionally substituted with one or two hydroxy groups; a group of Formula 1a or 1b as defined above; or a group CONR$^{20}$R$^{21}$, where R$^{20}$ and R$^{21}$ are hydrogen or lower alkyl, provided that Y may not be O or S when m is 1;

and pharmaceutically acceptable salts thereof.

In another aspect the invention relates to a method for the preparation of the novel compounds of Formula I.

In yet another aspect the invention relates to a pharmaceutical composition comprising a novel compound of Formula I together with a suitable pharmaceutically acceptable carrier or diluent.

In yet another aspect the invention relates to the use of a compound of Formula I or preparing a pharmaceutical composition for treatment of anxiety, agression, depression, sleep disturbances, migraine, negative symptoms of schizophrenia, psychoses, extrapyramidal side effects induced by conventional antipsychotics, abuse of drugs and substances of abuse or Parkinson's disease.

As already mentioned the present compounds show central 5-HT receptor antagonistic activity, in particular 5-HT$_2$ receptor antagonistic activity, and additionally, many of the compounds show antidopaminergic activity and, accordingly, they are useful in the treatment of CNS disorders, i.e. the above listed disorders.

DETAILED DESCRIPTION OF THE INVENTION

Some of the compounds of general Formula I may exist as optical isomers thereof and such optical isomers are also embraced by the invention.

In general Formula I, the term lower alkyl is intended to mean a C$_1$–C$_6$ straight chain or branched alkyl group such as methyl, ethyl, 1-propyl, 2-propyl, 1-butyl, 2-butyl, 2-methyl-2-propyl etc. Similarly, lower alkenyl and lower alkynyl designate C$_2$–C$_6$ straight chain or branched alkenyl or alkynyl groups. Lower alkoxy, lower alkylthio, lower alkylsulfonyl, lower alkylamino and lower dialkylamino similarly designate such groups wherein the alkyl moiety is a lower alkyl group as defined above. Cycloalkyl designates such a group having 3–7 carbon atoms and halogen means fluoro, chloro, bromo or iodo.

The Z groups COCH$_2$ and CSCH$_2$ may be incorporated in the ring of Formula 1 a in both directions.

The term "indicate an optional bond" is intended to mean that the dotted line may or may not represent a bond, i.e. that the compounds of Formula I are indoles or indolines.

The pharmaceutically acceptable acid addition salts of the compounds used in the invention are salts formed with non-toxic organic or inorganic acids. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids.

In Formula I, Ar is preferably phenyl optionally substituted with halogen, most preferably 4-fluorophenyl.

X is preferably a bond, CR$^c$R$^d$, O—CR$^a$R$^b$ or CR$^c$R$^f$—CR$^a$R$^b$ in particular CR$^c$R$^d$, O—CR$^a$R$^b$ or CR$^c$R$^f$—CR$^a$R$^b$, R$^a$ to R$^f$ preferably all being hydrogen, and especially O—CR$^a$R$^b$, wherein R$^a$ and R$^b$ each represent hydrogen.

The dotted line preferably designate a bond.

Preferably R$^1$ and R$^4$ are hydrogen. R$^2$ and R$^3$ are hydrogen, cyano or halogen, especially hydrogen bromo or chloro. R$^5$ is hydrogen or lower alkyl, optionally substituted with hydroxy, and R$^6$ is hydrogen or lower alkyl.

R$^7$ is preferably hydrogen or lower alkyl, most preferably hydrogen or methyl, or R$^7$ is linked to R$^9$ in order to form a 5–6 membered ring.

R$^8$ is preferably lower alkyl or a group of Formula 1a wherein n is 2, 3 or 4; W is O; U is N; V is NR$^{10}$, wherein R$^{10}$ is hydrogen, lower alkyl or lower alkenyl; and R$^9$ is hydrogen, lower alkyl or lower alkenyl; or R$^9$ is linked to R$^7$ in order to form a 5- or 6-membered ring, in particular a 5-membered ring, containing one nitrogen atom; or R$^8$ and R$^9$ together with the nitrogen atom to which they are attached form a group of Formula 1c wherein Y is O or a group CH—R$^{19}$ where R$^{19}$ is hydrogen or lower alkyl, or a group of Formula 1a as defined in the preceeding paragraph, or a group CONR$^{20}$R$^{21}$, where R$^{20}$ and R$^{21}$ are hydrogen or lower alkyl.

In a preferred subgroup of the compounds of the invention,

X is O—CH$_2$, CH$_2$—CH$_2$, CH$_2$ or a bond, in particular O—CH$_2$, CH$_2$—CH$_2$ or CH$_2$;

R$^1$ and R$^4$ are both hydrogen;

R$^2$ is selected from the group consisting of hydrogen, halogen, lower alkyl, lower alkoxy, hydroxy, nitro, lower alkylthio, lower alkylsulfonyl, lower alkyl- or dialkylamino, cyano, trifluoromethyl, trifluoromethylsulfonyloxy and trifluoromethylthio;

R$^3$ is hydrogen, or alternatively R$^3$ is selected from the R$^2$ substituents;

Ar is phenyl optionally substituted with halogen, in particular 4-fluorophenyl;

R$^6$ and R$^7$ are both hydrogen;

R$^8$ is a group of Formula 1a wherein n is 2, 3 or 4, in particular 2 or 3; W is O; U is N; V is NR$^{10}$, wherein R$^{10}$ is hydrogen or lower alkyl, in particular hydrogen; and R$^9$ is lower alkyl in particular methyl.

According to the invention the novel compounds of Formula I are prepared by a method comprising:

a) Alkylating an amine of the formula $HNR^8R^9$, wherein the substituents $R^8$ and $R^9$ are defined as described above except that $R^9$ may not be linked to $R^7$, with a compound of the following formula:

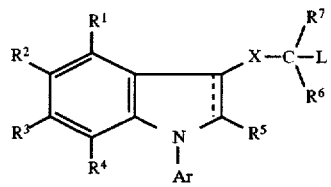

wherein $R^1$–$R^7$, X, Ar and the dotted line are as defined above, except that $R^7$ may not be a part of a ring, and the group L is a leaving group, such as a halogen atom or a tosyl or a mesyl group;

b) Reducing a compound of the following formula:

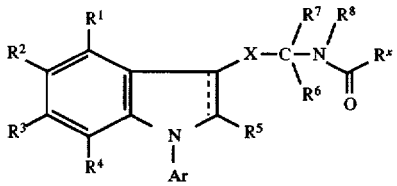

wherein $R^1$–$R^8$, X, Ar and the dotted line are as defined above, except that $R^8$ and $R^9$ may not together with the nitrogen atom form a group of Formula 1 c, and $R^x$ is an alkoxy or a lower alkyl group;

c) Alkylating a compound of the following formula:

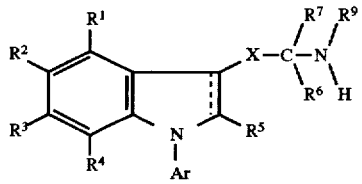

wherein $R^1$–$R^7$, $R^9$, X, Ar and the dotted line are as defined above, except that $R^8$ and $R^9$ may not together with the nitrogen atom form a group of Formula 1c, with an alkylating agent $R^8L$ in which $R^8$ is as defined above except that it may not be part of a ring, and L is a leaving group as defined above;

d) Reducing a compound of the following formula:

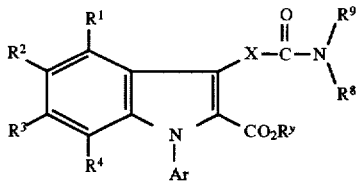

wherein $R^1$–$R^4$, $R^8$, $R^9$, X and Ar are as defined above, except that $R^9$ may not be linked to $R^7$, and $R^y$ is a lower alkyl group;

e) Reducing a compound of the following formula:

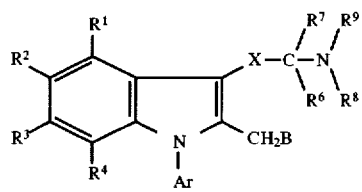

wherein $R^1$–$R^4$, $R^6$–$R^9$, X and Ar are as defined above and B is hydroxy or a halogen atom;

f) acylating an aminoalkyl derivative of the following formula:

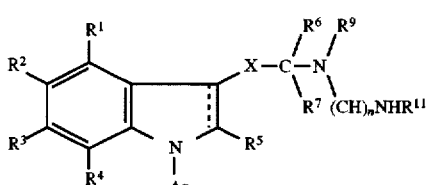

wherein $R^1$–$R^7$, $R^9$, X, Y, Ar, $R^{11}$, n and the dotted line are as defined above, except that $R^8$ and $R^9$ may not together with the nitrogen atom form a group of Formula 1c, with an acylating agent such as a carboxylic acid halogenide, anhydride or mixed anhydride, or a carbamoyl or thiocarbamoyl chloride, an isocyanate, isothiocyanate, or a substituted chloroformate;

g) Reacting a 1-unsubstituted indole derivative of the following formula:

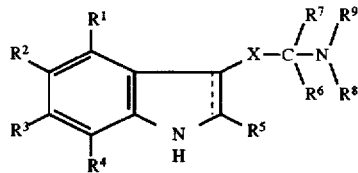

wherein $R^1$–$R^9$, X and the dotted line are as defined above, with an arylhalogenide, ArHal wherein Ar is as previously defined and Hal is iodine, bromine or chlorine;

h) Reacting bromo-indole derivative of the following formula:

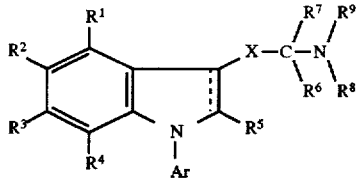

wherein one of the substituents $R^1$–$R^4$ is a bromine atom and the other substituents $R^1$–$R^4$ are as defined above and Ar, $R^5$–$R^9$, X and the dotted line are as defined above, with copper cyanide;

i) Reacting an indole derivative of the following formula:

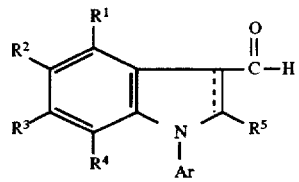

wherein $R^1$–$R^5$ and the dotted line are as described above, with a reducing agent and an amine of formula $HNR^8R^9$ wherein $R^8$ and $R^9$ are defined as defined above.

In method (a) the alkylation is performed at 20°–120° C. in an aprotic solvent such as acetone or isobutyl methyl ketone in the presence of free base (e.g. $K_2CO_3$ or triethylamine). The starting material II is prepared from the corresponding alcohol, which is prepared as described below, either by reaction with mesylchloride or tosylchloride or by reaction with thionylchloride or phosphorus oxychloride at conditions obvious to the chemist skilled in the art. The amines used as reactants are either commercially available or prepared by reaction of 1-(2-chloroethyl)-2-imidazolidinone or 1-(2-chloroethyl)-3-(2-propyl)-2-imidazolidinone with excess of appropriate amines at standard conditions.

The 3-(1-aryl-3-1H-indolyl)propanols used as starting material for the preparation of II are prepared as follows (Example 1). Ullmann arylation of substituted 3-(3-1H-indolyl)propanoic acids (prepared according to the metods described in GB Patent No. 1.220.628, *Chem. Abstr.* 1971, 75, 5690h, Renson, *Bull. Soc. Chim. Belg.* 1959, 68, 258–269 and Salituro et al, *J. Med. Chem.* 1990, 33, 2944–2946) with properly substituted aryliodides in NMP, DMF, HMPA or DMSO with potasium carbonate as base and catalyzed by copper, copper(I) iodide or copper(I) bromide at 150°–200° C. results in substituted 3-(1-aryl-3-1H-indolyl)propanoic acids. The acids thus obtained are reduced to substituted 3-(1-aryl-3-1H-indolyl)propanols by lithium aluminum hydride reduction at standard conditions.

The substitued 2-(1-aryl-3-1H-indolyloxy)ethanols used as starting materials for the preparation of II are prepared as follows (Example 2). Alkylation of substituted methyl 1-aryl-3-hydroxy-1H-indol-2-carboxylates (prepared from properly substituted N-(o-carboxyaryl)glycine according to methods described in Unangst et al., *J. Heterocyclic Chem.* 1984, 21, 709–714 and *J. Heterocyclic Chem.* 1987, 24, 811–815) with methyl bromoacetate results in corresponding methyl 2-(2-methoxycarbonyl-1-aryl-3-1H-indolyloxy) acetates, according to literature methods in Unangst et al., *J. Heterocyclic Chem.* 1984, 21, 709–714. These diesters are hydrolyzed and subsequently decarboxylated to give corresponding 2-(1-aryl-3-1H-indolyloxy)acetic acids by methods obvious to the chemist skilled in the art. The acids thus obtained are reduced to substituted 2-(1-aryl)-3-1H-indolyloxy]ethanols by lithium aluminum hydride reduction at standard conditions.

The 2-(3-1H-indolylthio)ethanols used as starting materials for the preparation of II are prepared as follows. 2,3-Dihydro-1-aryl-3-1H-indolones are reacted with 2-mercaptoacetic acid by heating of the reactants at reflux in toluene using a Dean-Stark apparatus with p-toluenesulfonic acid as a catalyst. (Example 10). The acids thus formed are subsequently reduced to the corresponding alcohols by lithium aluminium hydride reduction at standard conditions. The substituted 2,3-dihydro-1-aryl-3-1H-indolones used as starting materials are prepared by deprotection of substituted 3-acetoxy-1-arylindoles (prepared according to methods in Perregaard et al., *J. Med. Chem.* 1992, 35, 1092–1101) by heating in an aqueous solution of sodium sulfite (Example 4), according to the procedure described in Nenitzescu et al., *Chem. Ber.* 1958, 91, 1141–1145.

In method (b) the reductions of III are performed by using $LiAlH_4$, $AlH_3$, $B_2H_6$ or a $BH_3$ complex in an inert solvent as e.g. diethyl ether or tetrahydrofurane at 0° C. to 70° C. The starting material III is prepared as described below.

The carbamate proteceted or acylated compounds of Formula III in which $R^8$ is as defined above or is a hydrogen atom are prepared by reaction of a substituted 2,3-dihydro-1-aryl-3-1H-indolone with a properly substituted amino alcohol by heating the reactants at reflux in toluene using a Dean-Stark apparatus and p-toluenesulfonic acid as a catalyst (Example 5). Compounds of Formula III in which $R^8$ is a hydrogen atom are converted to compounds of Formula III in which $R^8$ is as defined above by reducing the acyl or carbamate group to an alkyl group and subsequently introduce appropriate carbamate or acyl groups by conventional methods. The substituted 2,3-dihydro-1-aryl-3-1H-indolones used as starting materials are prepared as described above. The substituted aminoalcohols used as reactants are prepared according to literature procedures for corresponding compounds. The carbamate protected or acylated B-amino alcohols containing a chiral center are prepared from corresponding chiral a-amino acids according to a one-pot procedure desribed by Correa et al., *Synth. Comm.* 1991, 21, 1–9. 2,2-Dimethyl-2-aminothanol is commercially available and was carbamate protected by standard procedures.

The alkylation in method (c) is performed at 20°–120° C. in an aprotic solvent such as acetone or isobutyl methyl ketone in the presence of a base (e.g. $K_2CO_3$ or triethylamine) and the starting material IV is prepared as described below.

The secondary amine IV is prepared by hydrolysis of a compound of Formula III using standard conditions for deprotection of carbamates or hydrolysis of tertiary amides obvious to the chemist skilled in the art or by reduction of compounds of Formula III in which $R^8$ is a hydrogen atom by conventional methods.

In methods (d) and (e) the reductions of V and VI are performed by using $LiAlH_4$, $AlH_3$, $B_2H_6$ or a $BH_3$ complex in inert solvents as e.g. diethyl ether or tetrahydrofurane at 0° C. to 70° C. The starting material is prepared by alkylation of substituted methyl 1-aryl-3-hydroxy-1H-indol-2-carboxylates, prepared as described above, with N,N-dimethyl-2-chloroacetamide according to the method described by Unangst et al., *J. Heterocyclic Chem.* 1987, 24, 811–815. The starting material for method (e) is prepared by reaction of compound IV with an alkyl or aryl sulfonylchloride in an aprotic solvent such as e.g. dichloromethane at –30° C. to 0° C.

Aminoalkyl derivatives of the Formula VII used in method (f) are prepared by alkylating a compound of the Formula IV with a halo-nitrile of the following formula: $hal(CH_2)_{n-1}CN$ in the presence of a base (e.g. $K_2CO_3$ or triethylamine) in an inert solvent such as acetone, MIBK or toluene at elevated temperature (30°–100° C.). The cyano group may be reduced according to standard procedures using e.g. $AlH_3$, $LiAlH_4$ or $B_2H_6$. The $R^{11}$ substituent is introduced by direct alkylation or by an acylation/reduction procedure, which is obvious to the chemist skilled in the art. Acylation of the thus obtained amino derivatives is accomplished by addition of an acylating agent at a low temperature (–20° to 30° C.) preferably in a chlorinated solvent (dichloromethane, chloroform, or 1,1,1-trichloroethane) and, if necessary, in the presence of a base to neutralize any acidic reaction product formed.

In method g) the Ullman arylation is conveniently performed as described above for the arylation of 3-(3-1H-indolyl)propanoic acid (Example 13). The starting material VIII in which X is a methylene group is prepared by acylation of the corresponding 1,3-unsubstituted indole with oxalyl chloride which subsequently is reacted with appropriate amines $HNR^8R^9$. The glyoxamide formed is reduced to the corresponding tryptamine by treatment with lithium aluminum hydride according to literature methods (Example 14) (Welstad et al. *J. Med. Chem.* 1967, 10, 1015–1021).

In method h) the Rosenmund-von Braun reaction is performed with copper cyanide in NMP, DMF or MSO at 150°–200° C. (Example 16). The starting material IX is prepared according to methods a)–g) and i).

In method i) the reductive amination is preferably performed in an one pot procedure using $NaCNBH_3$ and molecular sieves in an alcohol such as methanol, Borch et al. J. Am. Chem. Soc. 1971, 93, 2897–2904 (Example 12). Alternatively, the reaction can be performed in a two step procedure. In the first step the intermediate imine is formed by reaction of indole derivative, X, with an amine, $HNR^8R^9$, by methods obvious to the chemist skilled in the art. The intermediate imine is reduced with a reducing agent such as $NaBH_4$, $NaCNBH_3$ or $LiAlH_4$ in an appropriate solvent. The starting material of Formula X is prepared by Vilsmeyer formylation of a corresponding 3-unsubstituted indole using standard conditions (Example 11).

The 1-(2-chloroethyl)-2-imidazolidinone and 1-(2-chloroethyl)-3-(2-propyl)-2-imidazolidinone used as reactants above are prepared according to literature procedures in Johnston et al., J. Med. Chem. 1963, 6, 669–681, Perregaard et al., J. Med. Chem. 1992, 35, 1092–1101 and DE-A1 2035370, 1971., Chem. Abstr. 1971, 74, 87985z.

The acid addition salts of the compounds of the invention are easily prepared by methods well known in the art. The base is reacted with either the calculated amount of organic or inorganic acid in an aqueous miscible solvent, such as acetone or ethanol, with isolation of the salt by concentration and cooling, or reacted with an excess of the acid in an aqueous immiscible solvent such as ethyl ether or chloroform, with the desired salt separating directly. These salts may also be prepared by the classical method of double decomposition of appropriate salts.

The compounds of general Formula I and the pharmaceutically acceptable acid addition salts thereof may be administered in any suitable way, e.g. orally or parenterally, and the compounds may be presented in any suitable form for such administration, e.g. in the form of tablets, capsules, powders, syrups or solutions or dispersions for injection.

An effective daily dose of the a compound of general Formula I or a pharmaceutically acceptable salt thereof is from 0.05 to 500 mg, preferably 0.5 to 100 mg.

EXAMPLES

In the following the invention is further illustrated by way of examples which may in no way be construed as limiting for the invention.

$^1$H NMR spectra were recorded at 250 MHz on a Bruker AC 250 spectrometer. Deuterated chloroform (99.8% D) or dimethylsulfoxide (99.9% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, sex=sextet, h=heptet, dd=double doublet, m=multiplet. Content of water in crystalline compounds was determined by Karl Fischer titration. Results obtained by microanalyses were within ±0.4% of the theoretical values.

Mass spectra were obtained on a Quattro MS-MS system from VG Biotech, Fisons Instruments, Manchester, GB. The MS-MS system was connected to an HP 1050 modular HPLC system. A volume of 20–50 μl of the sample (0.1–0.05 mg/ml) dissolved in a mixture of acetonitrile:water:acetic acid=250:250:1 (v/v/v) was introduced via the autosampler at a flow of 30 μl/min into the Electrospray Source. Spectra were obtained at two sets of standard operating conditions. One to obtain molecular weight information ($MH^+$) and another to obtain fragmentation in the source (high cone voltage). The background was subtracted. The relative intensities of the molecular ions obtained in the fragmentation spectrum are given. If the relative intensity of the $MH^+$ ion not is given this ion was only obtained in the molecular weight spectra.

Example 1

3-[5-Chloro-1-(4-fluorophenyl)-3-1H-indolyl] propanol (1a)

A mixture of 3-(5-chloro-3-1H-indolyl)propanoic acid (17.5 g, 0.078 mol), 4-fluoroiodobenzene (20.8 g, 0.094 mol), CuI (2.4 g), $K_2CO_3$ (21.6 g, 0.16 mol) and N-methyl-2-pyrrolidone (0.20 L) was heated at 165° C. for 7 h. The reaction mixture was cooled to room temperature and water (0.25 L) was added. After acidification with concentrated hydrochloric acid, the mixture was extracted with diethyl ether (2×0.30 L) . The combined organic phases were washed with brine (3×0.40 L) and dried ($Na_2SO_4$). Evaporation of the solvents afforded crude 3-[5-chloro-1-(4-fluorophenyl)-3-1H-indolyl]propanoic acid (26 g) as an oil. The oil was dissolved in dry diethyl ether and added to a suspension of lithium aluminum hydride (15 g, 0.40 mol) in dry diethyl ether (0.20 L) over 30 min. After reflux for further 2 h the reaction mixture was cooled to 0° C. and carefully treated with water (15 ml), 4N aqueous NaOH (15 ml) and then water (75 mL). The resulting mixture was filtered and dried ($Na_2SO_4$). Evaporation of the solvents afforded the title compound (1a) as an oil (17.6 g, 74%). An analytical sample was crystallized from heptane: mp. 67°–69° C.; $^1$H NMR ($CDCl_3$) δ 1.55 (broad s, 1 H), 2.00 (qui, 2 H), 2.90 (t, 2 H), 3.75 (t, 2 H), 7.10 (s, 1 H), 7.15 (broad d, 1 H), 7.20 (t, 2 H), 7.35 (d, 1 H), 7.40 (dd, 2 H), 7.60 (broad s,1 H). Anal. ($C_{17}H_{15}ClFNO$) C, H, N.

Example 2

2-[5-Chloro-1-(4-fluorophenyl)-3-1H-indolyloxy] ethanol (2a)

A mixture of methyl 5-chloro-1-(4-fluorophenyl)-3-hydroxy-1H-indol-2-carboxylate (200 g, 0.62 mol), methyl 2-bromoacetate (125 g, 0.81 mol), $K_2CO_3$ (112 g, 0.81 mol) and acetone (2.0 L) was refluxed for 18 h. The mixture was cooled to room temperature and filtered, and the solvents were evaporated in vacuo. To the remaining oil (270 g) methanol (1.5 L) and 3N aqueous KOH (0.6 L) was added. After reflux for 1 h, the solution was cooled to room temperature and acidified by concentrated hydrochloric acid. The product thus precipitated was filtered off and dissolved in ethyl acetate and dried ($Na_2SO_4$). Evaporation of the solvents afforded 2-[2-carboxy-5-chloro-1-(4-fluorophenyl)-3-1H-indolyloxy]acetic acid (240 g) as an oil which was decarboxylated without further purification. A mixture of the crude dicarboxylic acid, copper (15 g) and N-methyl-2-pyrrolidone was refluxed for 1.5 h. The mixture was cooled to room temperature and water (2.0 L) was added. The product thus precipitated was filtered off and dissolved in ethyl acetate (1.5 L). The solution was washed with brine (3×1 L) and dried ($Na_2SO_4$). Evaporation of the solvents afforded the crude 2-[5-chloro-1-(4-fluorophenyl)-3-1H-indolyloxy]acetic acid (223 g) which was dissolved in dry diethyl ether (1.5 L). The thus formed solution was added to a suspension of lithium aluminum hydride (70 g, 1.9 mol) in dry diethyl ether (1.0 L) over 45 min. After reflux for additional 0.5 h, the reaction mixture was cooled to 0° C. and carefully treated with water (70 ml), 4N aqueous NaOH and then water (300 mL). The reaction mixture was filtered and dried ($Na_2SO_4$). Evaporation of the solvents afforded crystalline title compound (110 g, 55%). An analytical sample was recrystallized from diethyl ether: mp 118°–120° C.; $^1$H NMR ($CDCl_3$) δ 2.35 (broad s, 1 H),4.0 (t, 2 H), 4.15 (t, 2 H), 6.85 (s, 1 H), 7.10 (broad d, 1 H), 7.15 (t, 2 H), 7.40 (dd, 2 H), 7.65 (broad s, 1 H). Anal. ($C_{16}H_{13}ClF$—$NO_2$) C, H, N.

The following compound was prepared in a similar way:
2-|6-Chloro-1-(4-fluorophenyl)-3-1H-indolyloxy|ethanol (2b): mp 97°–98° C. (diethyl ether); $^1$H NMR ($CDCl_3$) δ 4.00 (t, 2 H), 4.15 (t, 2 H), 6.80 (s, 1H), 7.10 (d, 1H), 7.20 (t, 2 H), 7.40 (s, 1 H), 7.35 (dd, 2 H), 7.60 (d, 1 H). Anal. ($C_{16}H_{13}ClFNO_2$) C, H, N.

Example 3 (Method a)

1-|2-||2-|5-chloro-1-(4-fluorophenyl)-3-1H-indolyloxy|ethyl|methylamino|ethyl|-2-imidazolidinone Maleate (4b).

To a solution of 2-|5-chloro-1-(4-fluorophenyl)-3-1H-indolyloxy|ethanol (2a) (4.8, 0.016 mol) and triethylamine (5 mL) in dichloromethane (50 mL), a solution of methanesulfonyl chloride (1.9 mL, 0.025 mol) in dichloromethane (16 mL) was added at 0°–5° C. over 0.5 h. After stirring for 3 h at room temperature the reaction mixture was washed with water (2×100 mL), dried ($Na_2SO_4$) and the solvents were evaporated in vacuo. Excess of methanesulfonyl chloride was removed by concentrating the remaining oil with toluene in vacuo several times. The crude methanesulfonate of 2a (6.0 g, 0.016 mol) was used without further purification. A mixture of the crude methanesulfonate, 2-(methylamino)ethyl-2-imidazolidinone (4.9 g, 0.034 mol), $K_2CO_3$ (4.0 g, 0.029 mol) and methyl isobutyl ketone was refluxed for 18 h. After cooling to room temperature water (100 mL) was added and the resulting mixture was extracted with ethyl acetate (2×100 mL). The combined organic phases were washed with water (100 mL) and brine (100 mL), and dried ($Na_2SO_4$). Evaporation of the solvents and purification by column chromatography on silica gel (eluted with ethyl acetate/ethanol 5:1 containing 4% triethylamine) afforded the title compound (4.2 g, 61%) as an oil. The title compound crystallized as its maleate from ethyl acetate: mp 183°–185° C.; $^1$H NMR (DMSO-$d_6$) δ 2.85 (s, 3 H), 3.20–3.55 (m, 8 H), 3.65 (broad s, 2 H), 4.40 (broad t, 2 H) 6.05 (s, 2 H), 6.65 (broad s, 1 H), 7.2, (broad d, 1 H), 7.45 (t, 2 H), 7.55 (d, 1 H), 7.69 (7.55, 1 H), 7.60 (dd, 2 H), 7.70 (broad s, 1 H). MS (m/z) 431 (MH$^+$, 2), 170 (33), 113 (100); Anal. ($C_{22}H_{24}ClFN_4O_2 \cdot C_4H_4O_4$) C, H, N.

The following compounds were prepared in a similar way:
N,N-Dimethyl-3-[5-chloro-1-(4-fluorophenyl)-3-1H-indolyl]propylamine fumarate (3a): mp 172°–173° C. (ethanol); $^1$H NMR (DMSO-$d_6$) δ 2.00 (qui, 2 H), 2.50 (s, 6 H), 2.65–2.90 (m, 4 H), 6.50 (s, 2 H), 7.20 (broad d, 1 H), 7.40 (t, 2H), 7.45 (d, 1 H), 7.55 (s, 1 H), 7.60 (dd, 2 H), 7.70 (broad s, 1 H). MS (m/z) 331 (MH$^+$, 37), 286 (71), 258 (100), 251 (62); Anal. ($C_{19}H_{20}ClFN_2 \cdot C_4H_4O_4$) C, H, N.
1-|2-||3-|5-chloro-1-(4-fluorophenyl)-3-1H-indolyl]propyl] methylamino|ethyl]-2-imidazolidinone fumarate (3b): mp 132°–134° C. (ethanol); $^1$H NMR (DMSO-$d_6$) δ 1.80–2.00 (m, 2 H), 2.40 (s, 3 H), 2.55–2.80 (m, 6 H), 3.15–3.25 (m, 4H), 3.30–3.40 (m, 2 H), 6.30 (s, 1 H), 6.60 (s, 2 H), 7.20 (broad s, 1 H), 7.40 (t, 2 H), 7.45 (d, 1 H), 7.55 (s, 1 H), 7.60 (dd, 2 H), 7.70 (broad s, 1 H). MS (m/z) 429 (MH$^+$, 20), 286 (4), 113 (100); Anal. ($C_{23}H_{26}ClFN_4O \cdot C_4H_4O_4$) C, H, N.
5-Chloro-1-(4-fluorophenyl)-3-|3-(4-morpholinyl)propyl|-1H-indole maleate (3c): mp 144°–145° C. (ethyl acetate); $^1$H NMR (DMSO-$d_6$) δ 2.05 (qui, 2 H), 2.80 (t, 2H), 3.05–3.35 (m, 6H), 3.70–3.95 (m, 4 H), 6.05 (s,2 H), 7.20 (broad d, 1 H) 7.40 (t, 2 H), 7.50 (d, 1 H), 7.55 (s, 1 H), 7.60 (dd, 2 H), 7.75 (broad s, 1 H). MS (m/z) 373 (MH$^+$, 100), 286 (89), 258 (77), 251 (41) 100 (37); Anal. ($C_{21}H_{22}ClFN_2O \cdot C_4H_4O_4$) C, H, N.
5-Chloro-1-(4-fluorophenyl)-3-|3-(4-piperidinyl)propyl|-1H-indole hydrochloride (3d): mp 219°–212° C. (acetone); $^1$H NMR ($CDCl_3$) δ 1.70–2.00 (m, 4 H), 2.20–2.50 (m, 4 H), 2.50–2.75 (m, 2 H), 2.85 (t, 2 H), 2.95–3.05 (m, 2 H), 3.40–3.60 (m, 2 H), 7.15 (bd, 1H), 7.20 (t, 2 H), 7.35 (d, 1 H), 7.35 (s, 1 H), 7.40 (dd, 2 H), 7.50 (broad s, 1H). MS (m/z) 371 (MH$^+$, 100), 286 (44), 258 (38), 251 (22), 98 (30); Anal. ($C_{22}H_{24}ClFN_2 \cdot HCl$) C, H, N.
N,N-Dimethyl-2-[5-chloro-1-(4-fluorophenyl)-3-1H-indolyloxy]ethylamine sesqui fumarate (4a): mp 165°–167° C. (ethanol); $^1$H NMR (DMSO-$d_6$) δ 2.60 (s, 6 H), 3.15 (t, 2 H), 4.30 (t, 2 H), 6.60 (s, 3 H), 7.20 (broad d, 1 H), 7.40 (t, 2 H), 7.45 (s, 1 H), 7.50 (d, 1 H), 7.60 (dd, 2 H), 7.65 (broad s, 1 H). MS (m/z) 333 (MH$^+$), 72 (100); Anal. ($C_{18}H_{18}ClFN_2O \cdot 1.5(C_4H_4O_4)$)) C, H, N.
1-[2-||2-|5-Chloro-1-(4-fluorophenyl)-3-1H-indolyloxy] ethyl]ethylamino]ethyl]-2-imidazolidinone maleate (4c): mp 155°–157° C. (ethyl acetate); $^1$H NMR (DMSO-$d_6$) δ 1.30 (t, 3 H), 3.20–3.55 (m, 10 H), 3.55–3.80 (m, 2 H), 4.35–4.50 (m, 2 H), 6.05 (s, 2 H), 6.65 (s, 1 H), 7.25 (broad d, 1 H), 7.40 (t, 2 H), 7.50 (d, 1 H), 7.55 (s, 1 H), 7.60 (dd, 2 H), 7.70 (broad s, 1 H). MS (m/z) 445 (MH$^+$, 3), 184 (41), 113 (100); Anal. ($C_{23}H_{26}ClFN_4O_2 \cdot C_4H_4O_4$) C, H, N.
1-[2-[|2-|5-Chloro-1-(4-fluorophenyl)-3-1H-indolyloxy] ethyl](3-propynyl)amino]ethyl]-2-imidazolidinone oxalate (4d): mp 139°–141° C. (acetone); $^1$H NMR (DMSO-$d_6$) δ 2.75 (t, 2 H), 3.00 (t, 2 H), 3.10–3.30 (m, 5 H), 3.40 (t, 2 H), 3.65 (broad s, 2 H), 4.15 (t, 2 H), 6.25 (broad s, 1 H),7.20 (broad d, 1 H), 7.40 (t, 2 H), 7.45 (s, 1 H), 7.50 (d, 1 H), 7.55 (broad s, 1 H), 7.60 (dd, 2 H). MS (m/z) 455 (MH$^+$, 3), 194 (41), 113 (100); Anal. ($C_{24}H_{24}ClFN_4O_2 \cdot C_2H_2O_4$) C, H, N.
5-Chloro-1-(4-fluorophenyl)-3-[2-(1-piperidinyl)ethoxy]-1H-indole (4e): mp 82°–84° C. (n-heptane); $^1$H NMR ($CDCl_3$) δ 1.40–1.55 (m, 2 H), 1.55–1.70 (m, 4 H), 2.50 (t, 4H), 2.85 (t, 2 H), 4.15 (t, 2 H), 6.85 (s, 1 H), 7.15 (broad d, 1 H), 7.20 (t, 2 H), 7.30 (d, 1 H), 7.40 (dd, 2 H), 7.65 (broad s, 1 H). MS (m/z) 373 (MH$^+$, 1), 260 (2), 112 (100); Anal. ($C_{21}H_{22}ClFN_2O$) C, H, N.
5-Chloro-1-(4-fluorophenyl)-3-[2-(4-morpholinyl)ethoxy]-1H-indole maleate (4f): mp 185°–187° C. (ethyl acetate); $^1$H NMR (DMSO-$d_6$) δ 3.15–3.40 (m, 4 H), 3.40–3.60 (m, 2 H), 3.75–3.95 (m, 4 H), 4.40 (t, 2 H), 6.10 (s, 2 H), 6.25 (broad d, 1 H), 7.40 (t, 2 H), 7.50 (d, 1 H), 7.55 (s, 1 H), 7.60 (dd, 2 H), 7.70 (broad s, 1 H). MS (m/z) 375 (MH$^+$, 2), 114 (100); Anal. ($C_{20}H_{20}ClFN_2O_2 \cdot C_4H_4O_4$) C, H, N.
1-[2-||2-|6-chloro-1-(4-fluorophenyl)-3-1H-indolyloxy] ethyl]methylamino]ethyl]-2-imidazolidinone (4h): mp 100°–102° C. (diethyl ether); $^1$H NMR ($CDCl_3$) δ 2.40 (s, 3 H), 2.65 (t, 2 H), 2.90 (t, 2 H), 3.30–3.40 (m, 4 H), 3.45–3.60 (m, 2 H), 4.10 (t, 2 H), 4.50 (broad s, 1 H), 6.80 (s, 1 H), 7.10 (broad d, 1 H), 7.20 (t, 2 H), 7.35 (broad s, 1 H), 7.40 (dd, 2 H), 7.60 (d, 1 H); MS (m/z) 431 (MH$^+$, 3), 170 (65), 113 (100); Anal. ($C_{22}H_{24}ClFN_4O_2$) C, H, N.
1-|2-||2-|6-Chloro-1-(4-fluorophenyl)-3-1H-indolyloxy] ethyl]methylamino]ethyl]-3-(2-propyl)-2-imidazolidinone oxalate (4i): mp 165°–167° C. (acetone);

¹H NMR (DMSO-d₆) δ 1.00 (d, 6 H), 2.80 (s, 3H), 3.10–3.55 (m, 10 H), 3.90 (h, 1 H), 4.40 (m, 2 H), 7.15 (broad d, 1 H), 7.40 (t, 2 H), 7.45 (s, 1 H), 7.50 (broad s, 1 H), 7.60 (dd, 2 H), 7.65 (d, 1 H); MS (m/z) 473 (MH⁺, 10), 212 (62), 155 (100); Anal. ($C_{25}H_{30}ClFN_4O_2 \cdot C_2H_2O_4$) C, H, N.

N,N-Dimethyl-2-[6-chloro-1-(4-fluorophenyl)-3-1H-indolyloxy]ethylamine (4j): mp 66°–68° C.; ¹H NMR (CDCl₃) δ 2.40 (s, 6 H), 2.80 (t, 2 H), 4.15 (t, 2 H), 7.80 (s, 1 H), 7.10 (broad d, 1 H), 7.20 (t, 2 H), 7.35 (broad s, 1 H), 7.40 (dd, 2 H), 7.60 (d, 1 H). MS (m/z) 333 (MH⁺), 72 (100); Anal. ($C_{18}H_{18}ClFN_2O$) C, H, N.

1-[2-[1-[2-[5-Chloro-1-(4-fluorophenyl)-3-1H-indolyloxy]ethyl]-4-piperidinyl]ethyl]-2-imidazolidinone (4k): mp 134°–136° C.; ¹H NMR (CDCl₃) δ 1.20–1.50 (m, 5 H), 1.70–1.90 (m, 2 H), 2.05–2.20 (m, 2 H), 2.85 (t, 2 H), 2.95–3.05 (m, 2 H), 3.25 (t, 2 H), 3.40 (s, 4 H), 4.15 (t, 2 H), 4.45 (broad s, 1 H), 6.80 (s, 1 H), 7.15 (broad d, 1 H), 7.20 (t, 2 H), 7.30 (d, 1 H), 7.40 (dd, 2 H), 7.65 (broad s, 1 H). MS (m/z) 485 (MH⁺, 8), 224 (100), 99 (67); Anal. ($C_{26}H_{30}ClFN_4O_2$) C, H, N.

N-methyl-1-[2-[5-chloro-1-(4-fluorophenyl)-3-1H-indolyloxy]ethyl]4-piperidinecarboxamide (4n): mp 152°–154° C.; ¹H NMR (CDCl₃) δ 1.65–1.95 (m, 4 H), 2.00–2.25 (m, 3 H), 2.80 and 2.85 (two singlets due to two rotamers, 3 H), 2.85 (t, 2 H), 3.00–3.10 (m, 2 H), 4.15 (t, 2 H), 5.50 (broad s, 1 H), 6.80 (s, 1 H), 7.15 (broad d, 1 H), 7.20 (t, 2 H), 7.30 (d, 1 H), 7.40 (dd, 2 H), 7.65 (broad s, 1 H). MS (m/z) 430 (MH⁺, 7), 169 (100), 110 (52) Anal. ($C_{23}H_{25}ClFN_3O_2$) C, H, N.

6-Chloro-1-(4-fluorophenyl)-2-(1-pyrrolidinyl)ethoxy-1H-indole (4O): mp 60°–62° C.; ¹H NMR (CDCl₃) δ 1.75–1.90 (m, 4 H), 2.60–2.75 (m, 4 H), 3.00 (t, 2 H), 4.15 (t, 2 H), 6.80 (s, 1 H), 7.10 (broad d, 1 H), 7.20 (t, 2 H), 7.35 (broad s, 1 H), 7.40 (dd, 2 H), 7.60 (d, 1 H). MS (m/z) 359 (MH⁺), 98 (100); Anal. ($C_{20}H_{20}ClFN_2O$) C, H, N.

6-Chloro-1-(4-fluorophenyl)-2-(1-piperidinyl)ethoxy-1H-indole (4p): mp 67°–69° C.; ¹H NMR (CDCl₃) δ 1.40–1.55 (m, 2 H), 1.55–1.70 (m, 4 H), 2.50–2.65 (m, 4 H), 2.85 (t, 2 H), 4.20 (t, 2 H), 7.80 (s, 1 H), 7.10 (broad d, 1 H), 7.20 (t, 2 H), 7.35 (broad s, 1 H), 7.40 (dd, 2 H), 7.60 (d, 1 H). MS (m/z) 373 (MH⁺), 112 (100); Anal. ($C_{21}H_{22}ClFN_2O$) C, H, N.

N,N-Dimethyl-2-[5-chloro-1-(4-fluorophenyl)-3-1H-indolylthio]ethylamine hydrochloride (4q): mp 200°–202° C. (acetone); ¹H NMR (DMSO-d₆) δ 2.70 (s, 6 H), 3.05–3.30 (m, 4 H), 7.30 (dd, 1 H), 7.45 (t, 2 H), 7.55 (d, 1 H), 7.75 (broad s, 1 H), 7.70 (dd, 2 H), 8.10 (s, 1 H). MS (m/z) 349 (MH⁺, 1), 276 (100), 104 (34), 58 (64); ($C_{18}H_{18}ClFN_2S \cdot HCl$) C, H, N.

1-[2-[[2-[5-Chloro-1-(4-fluorophenyl)-3-1H-indolylthio]ethyl]methylamino]ethyl]-2-imidazolidinone (4r) mp 65°–67° C. (acetone); ¹H NMR (CDCl₃) δ 2.95 (s, 3 H), 3.35–3.75 (m, 12 H), 4.90 (s, 1 H), 7.35 (t, 2 H), 7.40 (bd, 1 H), 7.50 (d, 1 H), 7.65 (d, 1 H), 7.75 (s, 1 H), 7.85 (broad s, 1 H); MS (m/z) 447 (MH⁺, 4), 276 (100), 202 (13), 113 (51); Anal. ($C_{22}H_{24}ClFN_4OS \cdot HCl \cdot 0.85H_2O$) C, H, N.

1-[2-[[5-chloro-1-(4-fluorophenyl)-3-1H-indolylmethyl]methylamino]ethyl]-2-imidazolidinone (4s): mp 141°–143° C. (ethyl acetate); ¹H NMR (CDCl₃) δ 2.30 (s, 3 H), 2.60 (t, 2 H), 3.25–3.50 (m, 6 H), 3.70 (s, 2 H), 4.50 (broad s, 2 H), 7.10–7.25 (m, 4 H), 7.35 (d, 1 H), 7.40 (dd, 2 H), 2.80 (broad s, 1 H); MS (m/z) 401 (MH⁺, 3), 258 (64), 223 (100), 222 (80), 162 (60). Anal. ($C_{21}H_{22}ClFN_4O$) C, H, N.

1-[4-[[5-chloro-1-(4-fluorophenyl)-3-1H-indolylmethyl]methylamino]butyl]-2-imimidazolidinone oxalate (4t)

:mp 155°–157° C. (acetone); ¹H NMR (DMSO-d₆) δ 1.80–1.95 (m, 4 H), 2.80 (s, 3 H), 3.10–3.35 (m, 6 H), 3.35–3.50 (m, 2H), 4.60 (s, 2 H), 6.65–6.75 (m, 1 H), 7.20 (broad d, 1 H), 7.35–7.50 (m, 3 H), 7.60 (dd, 2 H), 7.70 (dd, 1 H), 7.80 (broad s, 1 H); MS (m/z) 429 (MH⁺), 258 (100), 223 (27), 141 (91). Anal. ($C_{23}H_{26}ClFN_4O \cdot C_2H_2O_4$) C, H, N.

1-[3-[[2-[5-chloro-1-(4-fluorophenyl)-3-1H-indolyl]ethyl]methylamino]propyl]-2-imidazolidinone hydrochloride (4u): mp 171°–173° C. (acetone); ¹H NMR (CDCl₃) δ 2.10–2.30 (m, 2 H), 2.90 (s, 3 H), 3.05–3.60 (12 H), 4.60 (broad s, 1 H), 7.15–7.35 (m, 5 H), 7.40 (dd, 2 H), 7.60 (broad s, 1 H); MS (m/z) 429 (MH⁺, 2), 272 (34), 237 (20), 127 (100), 99 (44). Anal. ($C_{23}H_{26}ClFN_4O \cdot HCl$) C, H, N.

1-[2-[[2-[5-chloro-1-(4-fluorophenyl)-3-1H-indolyl]ethyl]methylamino]ethyl]-2-imidazolidinone maleate (4v): mp 137°–139° C.; ¹H NMR (DMSO-d₆) δ 2.95 (s, 3 H), 3.10–3.55 (m, 12 H), 6.05 (s, 2 H), 6.65 (broad s,1 H), 7.25 (broad d, 1 H), 7.40–7.55 (m, 3 H), 7.60 (dd, 2 H), 7.65 (s, 1 H), 7.65 (broad s, 1 H); MS (m/z) 415 (MH⁺), 272 (33), 237 (28), 113 (100). Anal. ($C_{22}H_{24}ClFN_4O \cdot C_4H_4O_4$) C, H, N.

Example 4

5-Chloro-2,3-dihydro-1-(4-fluorophenyl)-3-1H-indolone (5)

To a mixture of $Na_2SO_3 \cdot 7H_2O$ (90 g, 0.36 mol) and water (1.8 L) was at 60° C. added ethanol (1.5 L) and 3-acetoxy-5-chloro-1-(4-fluorophenyl)-1H-indole (60 g, 0.20 mol). The resulting mixture was refluxed for 1 h and after stirring at room temperature for further 18 h the precipitate was filtered off, washed with water (300 ml) at 60° C. and dried in vacuo over night at 60° C. affording the title compound (44.3 g, 85%): mp 99°–101° C.; ¹H NMR (CDCl 3) δ 4.20 (s, 2 H), 7.10 (s, 1 H), 7.10 (t, 2 H), 7.25 (dd, 2 H), 7.40 (broad d, 1 H), 7.60 (broad s, 1 H). Anal. ($C_{14}H_9ClFNO$) C, H, N.

Example 5 (Method b)

(S)-N, N-Dimethyl-2-[5-chloro-1-(4-fluorophenyl)-3-1H-indolyloxy]-1-methylethylamine Oxalate (6a)

A mixture of 5-chloro-2,3-dihydro-1-(4-fluorophenyl)-3-1H-indolone (5) (1.1 g, 5.7 mmol), (S)-N-Ethoxycarbonylalaninol (2.9 g, 17 mmol), p-toluenesulfonic acid (0.8 g) and toluene (50 mL) was refluxed for 18 h. Evaporation of the solvents and purification by column chromatography (eluted with ethyl acetate/heptane 1:2) afforded the crude (S)-N-methyl-2-[5-chloro-1-(4-fluorophenyl)-3-1H-indolyloxy]-N-ethoxycarbonyl-1-methylethylamine as an oil (1.1 g). The crude carbamate was dissolved in dry diethyl ether (50 mL) and added to a suspension of lithium aluminum hydride (0.5 g, 13 mmol) in dry diethyl ether (50 mL). After reflux for 2 h the reaction mixture was cooled to 0° C. and carefully treated with water (1 mL) and 4N aqueous NaOH (1 mL). The precipitate was filtered off and extracted with dichloromethane (3×50 mL). The combined organic phases were dried ($Na_2SO_4$) and the solvents were evaporated affording the crude N-methyl compound as an oil (0.6 g). A solution of methyl chloroformate (0.20 g, 2.1 mmol) in dichloromethane (20 mL) was added to a mixture of the crude N-methyl compound, $K_2CO_3$ (0.3 g) and dichloromethane (20 mL). After reaction for 3.5 h the reaction mixture was filtered and the solvents were evaporated. The remaining oil was suspended in dry diethyl ether (20 mL) and added to a suspension of lithium aluminum hydride in dry diethyl ether (20 mL). The resulting mixture was refluxed for 2 h and subsequently cooled to 0° C. The reaction mixture was treated with water (0.5 mL) and 4N aqueous NaOH (0.5 mL). The precipitate was filtered off and extracted with dichloromethane (3×50 mL). The combined organic phases were dried ($Na_2SO_4$) and the solvents were evaporated affording an oil. The product was purified by column chromatography (eluted with ethanol/ethyl acetate 6:1 containing 4% triethylamine) giving the title compound 6a (0.30 g, 23%) as an oil which was precipitated as its oxalate in acetone: mp 161°–163° C.; $[\alpha]^{22}_D$+11.4° (c 1.0; $CH_3OH$); $^1H$ NMR (DMSO-$d_6$) δ 1.35 (d, 3 H), 2.80 (s, 6 H), 3.80 (sex, 1 H), 4.30 (m, 2 H), 7.20 (broad d, 1 H), 7.40 (t, 2 H), 7.50 (d, 1 H), 7.55 (s, 1 H), 7.60 (dd, 2 H), 7.75 (broad s, 1 H). MS (m/z) 347 (MH+), 260 (3), 86 (100); Anal. ($C_{19}H_{20}ClFN_2O.C_2H_2O_4$) C, H, N.

The following compounds were prepared accordingly:

(R)-N,N-Dimethyl-2-[5-chloro-1-(4-fluorophenyl)-3-1H-indolyloxy]-1-methylethylamine oxalate (6b): mp 162°–164° C. (acetone); $[\alpha]^{22}_D$-7.0° (c 1.0; $CH_3OH$); $^1H$ NMR (DMSO-$d_6$) 1.35 (d, 3 H), 2.80 (s, 6 H), 3.80 (sex, 1 H), 4.30 (m, 2 H), 7.20 (broad d, 1 H), 7.40 (t, 2 H), 7.50 (d, 1 H), 7.55 (s, 1 H), 7.60 (dd, 2 H), 7.75 (broad s, 1 H). MS (m/z) 347 (MH+), 260 (3), 86 (100); Anal. ($C_{19}H_{20}ClFN_2O.C_2H_2O_4$) C, H, N.

N,N-Dimethyl-1,1-dimethyl-2-[5-chloro-1-(4-fluorophenyl)-3-1H-indolyloxy]ethylamine oxalate (6c): mp 156°–157° C. (acetone); $^1H$ NMR (DMSO-$d_6$) δ 1.45 (s, 6 H), 2.80 (s, 6 H), 4.20 (s, 2 H), 7.25 (broad d, 1 H), 7.40 (t, 2 H), 7.50 (d, 1 H), 7.55 (s, 1 H), 7.60 (dd, 2 H), 7.80 (broad s, 1 H). MS (m/z) 361 (MH+), 260 (41), 100 (100); Anal. ($C_{20}H_{22}ClFN_2O.C_2H_2O_4$) C, H, N.

Example 6 (Method b)

(S)-1-Methyl-2-pyrrolidinylmethoxy-5-chloro-1-(4-fluorophenyl)-1H-indole Oxalate (7a).

A mixture of 5-chloro-2,3-dihydro-1-(4-fluorophenyl)-3-1H-indolone (5) (1.0 g, 3.8 mmol), (S)-N-ethoxycarbonylprolinol (2.0 g, 12 mmol), p-toluenesulfonic acid (5.0 g) and toluene (500 mL) was refluxed for 18 h. Evaporation of the solvents and purification by column chromatography (eluted with ethyl acetate/heptane 1:2) afforded the crude (S)-1-methoxycarbonyl-2-pyrrolidinylmethoxy-5-chloro-1-(4-fluorophenyl)-1H-indole as an oil (1.1 g). A solution of the crude carbamate in dry diethyl ether (20 mL) was added to a suspension of lithium aluminum hydride (0.8 g, 21 mmol) in dry diethyl ether (30 mL). After reflux for 0.5 h the reaction mixture was cooled to 0° C. and treated with water (1 mL) and 4N aqueous NaOH (1 mL). The precipitate was filtered off and extracted with dichloromethane (3×50 mL). The combined organic phases were dried ($Na_2SO_4$) and the solvents were evaporated affording the title compound (7a) as an oil (1 g). Purification by column chromatography on silica gel (eluted with ethyl acetate/heptane 1:1 containing 4% triethylamine) afforded pure title compound (7a) (0.7 g, 51%) as an oil. The title compound was precipitated as its oxalate in acetone: mp 177°–179° C.; $[\alpha]^{22}_D$+8.2° (c 1.0; $CH_3OH$); $^1H$ NMR (DMSO-$d_6$) δ 1.75–2.10 (m, 3 H), 2.15–2.35 (m, 1 H), 2.90 (s, 3 H), 3.00–3.15 (m, 1 H), 3.50–3.65 (m, 1 H), 3.70–3.80 (m, 1 H), 4.35 (d, 2 H), 7.20 (broad d, 1 H), 7.40 (t, 2 H), 7.50 (d, 1 H), 7.55 (s, 1 H), 7.60 (dd, 2 H), 7.70 (broad s, 1 H). MS (m/z) 359 (MH+, 1), 260 (4), 98 (100); Anal. ($C_{20}H_{20}ClFN_2O.C_2H_2O_4$) C, H, N.

The following compound was prepared accordingly:
(S)-1-Methyl-2-pyrrolidinylmethoxy-5-chloro-1-(4-fluorophenyl)-1H-indole oxalate (7b): mp 176°–178° C.; $[\alpha]^{22}_D$-7.5° (c 1.0; $CH_3OH$); $^1H$ NMR (DMSO-$d_6$) δ 1.75–2.10 (m, 3 H), 2.15–2.35 (m, 1 H), 2.90 (s, 3 H), 3.00–3.15 (m, 1 H), 3.50–3.65 (m, 1 H), 3.70–3.80 (m, 1 H), 4.35 (d, 2 H), 7.20 (broad d, 1 H), 7.40 (t, 2 H), 7.50 (d, 1 H), 7.55 (s, 1 H), 7.60 (dd, 2 H), 7.70 (broad s, 1 H). MS (m/z) 359 (MH+), 260 (4), 98 (100); Anal. ($C_{20}H_{20}ClFN_2O.C_2H_2O_4$) C, H, N.

Example 7 (Method c)

(R)-1-[2-[2-[5-Chloro-1-(4-fluorophenyl)-3-1H-indolyloxymethyl]-1-pyrrolidinyl]ethyl]-2-imidazolidinone Oxalate (8a)

A mixture of (R)-1-methoxycarbonyl-2-pyrrolidinylmethoxy-5-chloro-1-(4-fluorophenyl)-1H-indole (3.6 g, 0.016 mol) (prepared as the corresponding S-isomer in Example 6), 1-propanol (75 mL), water (50 mL) and NaOH (2.5 g) was refluxed for 6 days. The volatile solvents were evaporated in vacuo and water (250 mL) was added. The resulting mixture was extracted with diethyl ether (2×250 mL) and the combined organic phases were dried ($MgSO_4$). Evaporation of the solvents afforded the crude (R)-2-pyrrolidinylmethoxy-5-chloro-1-(4-fluorophenyl)-1H-indole (3.3 g) as an oil. A mixture of the crude (R)-2-pyrrolidinylmethoxy-5-chloro-1-(4-fluorophenyl)-1H-indole, 1-(2-chloroethyl)-2-imidazolidinone (2.1 g), $K_2CO_3$ (2.0 g), KI (0.3 g) and methyl isobutyl ketone (50 mL) was refluxed for 18 h. After cooling to room temperature the reaction mixture was poured into water (100 mL) and extracted with ethyl acetate (2×100 mL). The combined organic phases were washed with brine, dried ($Na_2SO_4$) and the solvents were evaporated in vacuo. The remaining oil, 4.0 g, was purified by column chromatography on silica gel (eluent ethyl acetate/ethanol 9:1 containing 4% triethylamine) affording the pure title compound (0.9 g, 12%) as an oil, that precipitated as oxalate in acetone: mp 84°–87° C.; $^1H$ NMR (DMSO-$d_6$) δ 1.70–2.30 (m, 4H), 2.90–3.85 (m, 11 H), 4.20–4.40 (m, 2H), 6.50 (s, 1 H), 7.20 (broad d, 1 H), 7.40 (t, 2H), 7.45 (d, 1 H), 7.50 (s, 1 H), 7.60 (dd, 2H), 7.65 (broad s, 1 H). Anal. ($C_{24}H_{26}ClFN_4O_2.C_2H_2O_4$) C, H, N; MS (m/z) 457 (MH+, 3), 196 (62), 113 (100).

The following compound was prepared accordingly:
(S)-1-[1-methyl-2-[[2-[5-chloro-1-(4-fluorophenyl)-3-1H-indolyloxy]ethyl]methylamino]ethyl]-2-imidazolidinone oxalate (8b): mp 102°–104° C.; $^1H$ NMR (DMSO-$d_6$) δ 1.35 (d, 3 H), 2.75 (s, 3 H), 3.10–3.30 (m, 4 H), 3.30–3.50 (m, 4 H), 3.75–3.90 (m, 1 H), 4.20–4.35 (m, 2H), 6.50 (s,1 H), 7.20 (broad d, 1 H), 7.40 (t, 2 H), 7.45 (s, 1 H), 7.50 (d, 1H), 7.60 (dd, 2 H), 7.65 (broad s, 1 H). MS (m/z) 445 (MH+, 2), 184 (19), 113 (100); Anal. ($C_{23}H_{26}ClFN_4O_2.C_2H_2O_4$) C, H, N.

Example 8 (Method d)

N,N-Dimethyl-2-[5-chloro-1-(4-fluorophenyl)-2-hydroxymethyl-3-1H-indolyloxy]ethylamine Hydrochloride (9)

A solution of N,N-dimethyl-2-chloroacetamide (28 g) in acetone (300 mL) was added dropwise during 1 hour to a mixture of 5-chloro-1-(4-fluorophenyl)-3-hydroxy-1H-indole-2-carboxylic acid methyl ester (64 g) (prepared according to the method of Unangst et al. *J.Heterocyc.Chem.* 1984, 21, 709–714 and 1987, 24, 811–815) and potassium carbonate (40 g) in acetone (500 mL) kept at reflux. The mixture was refluxed for another 3 hours and subsequently

17 worked-up. The resulting crude acetamide derivative crystallized from cyclohexane. Yield 72 g. Mp: 124°–125° C. To a suspension of LiAlH$_4$ pellets (10 g) in dry THF (200 mL) kept at gentle reflux was added dropwise a solution of the acetamide derivative (35 g) in dry THF (300 mL). After reflux for 2 hours the mixture was cooled on an ice bath and excess LiAlH$_4$ was hydrolyzed by cautiously adding a mixture of 10% water in THF. Inorganic salts were filtered off and the solvent evaporated in vacuo leaving the title compound as a viscous oil. Yield: 19 g. The hydrochloric acid salt of the title compound 9 crystallized from acetone by addition of a solution of hydrogenchloride gas in diethyl ether. mp 185°–186° C.; $^1$H NMR (DMSO-d$_6$) δ 2.90 (s, 6H), 3.60 (t, 2H), 4.40 (s, 2H), 4.45 (t, 2H), 7.05 (d, 1H), 7.10 (dd, 1H), 7.40 (t, 2H), 7.55 (dd, 2H), 7.85 (d, 1H). MS (m/z) 363 (MH$^+$), 72 (100); Anal (C$_{19}$H$_{20}$ClFN$_2$O$_2$·HCl) C, H, N.

Example 9 (Method e)

N,N-Dimethyl-2-[5-chloro-1-(4-fluorophenyl)-2-methyl-3-1H-indolyloxy]ethylamine Oxalate (10)

Triethylamine (1 g) was added to a solution of N,N-dimethyl-2-[5-chloro-1-(4-fluorophenyl)-2-hydroxymethyl-3-1H-indolyloxy]ethylamine 9 (3 g) in dichloromethane (100 mL) cooled to –10° C. A solution of methanesulfonylchloride (1.1 g) in dichloromethane (25 mL) was added dropwise at –10° to 0° C. After stirring for ½ h at 0° C. ice cooled water was added and the organic phase was subsequently worked up leaving the 2-chloromethylindole derivative as an oil. This oil was used immediately without further purification. To a solution of the oil in dry THF was added LiAlH$_4$ (1 g). After refluxing for 1 h, the mixture was cooled on an ice bath and excess LiAlH$_4$ was hydrolyzed by cautiously adding a mixture of 10% water in THF. Inorganic salts were filtered off and the solvent evaporated in vacuo. The resulting viscous oil was subjected to column chromatography on silica gel (eluted with 4% triethylamine in ethyl acetate) yielding the pure title compound as an oil. Yield: 0.6 g. The oxalic acid salt 10 crystallized from 2-propanol. mp 236°–237° C.; $^1$H NMR (DMSO-d$_6$) δ 2.15 (s, 3H), 2.85 (s, 6H), 3.40 (t, 2H), 4.35 (t, 2H), 7.00 (d, 1H), 7.05 (dd, 1H), 7.40 (t, 2H), 7.45 (dd, 2H), 7.70 (d, 1H). MS (m/z) 347 (MH$^+$), 274 (6), 223 (36), 222 (20), 72 (100); Anal (C$_{19}$H$_{20}$ClFN$_2$O·C$_2$H$_2$O$_4$) C, H, N.

Example 10

2-(5-Chloro-3-1H-indolylthio)ethanol (11)

A mixture of 5-chloro-2,3-dihydro-1-(4-fluorophenyl)-3-1H-indolone (5) (25.0 g, 0.10 mol), mercaptoacetic acid (25 g, 0.27 mol), p-toluenesulfonic acid (5.0 g) and toluene (500 mL) was refluxed for 18 h. Evaporation of the solvents afforded crude 2-[5-chloro-1-(4-fluorophenyl)-3-1H-indolylthio]acetic acid which was isolated as an oil and used without further purification. A solution of the crude acid in dry tetrahyrofuran (200 mL) was added to a suspension of lithium aluminum hydride (7.5 g, 0.20 mol) in dry tetrahyrofuran (200 mL) during 15 min. After reflux for 1 h the reaction mixture was cooled to 0° C. and carefully treated with water (5 mL) and 28% aqueous NaOH (5 mL). The precipitate was filtered off and extracted with dichloromethane (3×500 mL). The combined organic phases were dried (MgSO$_4$) and the solvents were evaporated affording the title compound (11) as an oil (25 g). Purification by column chromatography on silica gel (eluted with ethyl acetate/heptane 1:2) afforded pure title compound (11) (12 g, 40%) as an oil: $^1$H NMR (CDCl$_3$) δ 2.10–2.50 (broad s, 1 H),

18

2.95 (t, 2 H), 3.70 (t, 2 H), 7.20 (broad d, 1 H), 7.25 (t, 2 H), 7.35 (d, 1 H), 7.40 (dd, 2 H), 7.45 (s, 1 H), 7.80 (broad s, 1 H). Anal. (C$_{16}$H$_{13}$ClFNS) C, H, N.

Example 11

5-chloro-1-(4-fluorophenyl)indol-3-carbaldehyde (12a)

Phosphorus oxychloride (12.5 g, 0.081 mol) was added to N,N-dimethylformamide (29.5 g, 0.19 mol) at 0°–5° C. After stirring for 10 minutes a solution of 5-chloro-1-(4-fluorophenyl)indole (20 g, 0.081 mol) in N,N-dimethylformamide (50 mL) was added at 0°–5° C. The reaction mixture was stirred for 0.5 h and subsequently poured into ice. The resulting mixture was made alkaline with concentrated NaOH and after stirring for 1 h at room temperature the mixture was extracted with diethyl ether (2×250 mL). The combined organic phases were dried (Na$_2$SO$_4$), the solvents evaporated and the remaining oil was purified by column chromatography (eluted with ethyl acetate/heptane 1:1) affording pure title compound 20.1 g (90%) which crystalized from heptane: mp 152°–154° C.; $^1$H NMR (CDCl$_3$) δ 7.20–7.35 (m, 4 H), 7.50 (dd, 2 H), 7.85 (s, 1 H), 8.35 (s, 1 H), 10.05 (s, 1 H). Anal. (C$_{15}$H$_9$NO) C, H, N.

Example 12 (Method i)

N,N-Dimethyl-[5-chloro-1-(4-fluorophenyl)-3-1H-indolyl]methylamine Maleate (13a)

A mixture of 5-chloro-1-(4-fluorophenyl)indol-3-carbaldehyde (2.5 g, 0.0091 mol) dimethylamine hydrochloride (1.5 g, 0.018 mol), 3 Å molecular sieves (5 g) and methanol (50 mL) was stirred at room temperature for 1 h. Sodium cyanoborohydride (0.6 g, 0.095 mol) was added and the mixture was stirred for 24 h at room temperature. Further 3 Å molecular sieves (5 g) and sodium cyanoborohydride (0.6 g, 0.095 mol) was added and the mixture stirred for further 24 h at room temperature. The precipitate was filtered off and the solvents evaporated. The remaining oil was purified by column chromatography (eluted with ethyl acetate/heptane 1:1 containing 4% triethylamine) affording pure title compound as an oil (2.1, 76%). The maleate of 13a was crystalized from ethanol: mp 174°–177° C.; $^1$H NMR (DMSO-d$_6$) δ 2.80 (s, 6 H), 4.50 (s, 2 H), 6.05 (s, 2 H), 7.30 (broad d, 1 H), 7.40–7.55 (m, 3 H), 7.70 (dd, 2 H), 7.95 (s, 1 H), 8.10 (broad s, 1 H); MS (m/z)303 (MH$^+$), 258 (20), 223 (61), 222 (100), 162 (70), 127 (61). Anal. (C$_{17}$H$_{16}$ClFN$_2$·C$_4$H$_4$O$_4$) C, H, N.

The following compound was prepared in a similar way:
N-methyl-[5-chloro-1-(4-fluorophenyl)-3-1H-indolylmethyl]amine hydrochloride (13b): mp 236°–238° C. (acetone); $^1$H NMR (DMSO-d$_6$) δ 2.55 (s, 3 H), 4.35 (s, 2H), 7.25 (broad d, 1 H), 7.40–7.55 (m, 3 H), 7.65 (dd, 2 H), 7.95 (s, 1 H), 8.05 (broad s, 1 H) ; MS (m/z) 289 (MH$^+$, 1), 258 (14), 223 (45) 222 (100), 162 (62) 127 (28). Anal. (C$_{16}$H$_{14}$ClFN$_2$·HCl) C, H, N.

Example 13 (Method g)

N-benzyl-N-methyl-2-[5-chloro-1-(4-fluorophenyl)-3-1H-indolyl]ethylamine (14a)

To a solution of 5-chloroindole (20 g, 0.13 mol) in dry diethyl ether (200 mL) was added a solution of oxalylchloride (20 g, 0.16 mol) in dry diehtyl ether (200 mL) at 0°–5° C. After stirring for 0.5 h at 0°–5° C. was added a solution of benzylmethylamine (24 g, 0.20 mol) in dry diethyl ether at 0°–5° C. and triethylamine was slowly added to pH at 8–9. Water and ethyl acetate (500 mL) was added and the organic phase was washed with brine and dried (Na$_2$SO$_4$). Evaporation of the solvents afforded the crude N-benzyl-N-methyl-2-(5-chloro-1-(4-fluorophenyl)-3-1H-indolyl)-2-oxoacetamide (19.1 g) as an oil. A solution of the crude N-benzyl-N-methyl-2-(5-chloro-1-(4-fluorophenyl)-3-1H-indolyl)-2-oxoacetamide (20.1 g, 0.058 mol) in dry tetrahydrofuran (200 mL) was added to a suspension of lithium aluminium hydride (5.4 g, 0.14 mol) in tetrahydrofuran (100 mL). After heating at reflux for 2.5 h the reaction mixture was cooled to 0° C. and treated with water (6 mL) and 4N aqueous NaOH (6 mL). The precipitate was filtered off and extracted with dichloromethane (3×200 mL). The combined organic phases were dried (Na$_2$SO$_4$) and the solvents were evaporated. The remaining oil was purified by column chromatography (eluted with ethyl acetate) affording N-benzyl-N-methyl-2-(5-chloro-3-1H-indolyl)ethylamine (16 g) as an oil: $^1$H NMR (CDCl$_3$) δ 2.30 (s, 3 H), 2.65–2.80 (m, 2 H), 2.85–3.00 (m, 2 H), 3.60 (s, 2 H), 6.95 (broad s, 1 H), 7.05–7.20 (m, 2 H), 7.15–7.35 (m, 5), 7.45 (broad s,1 H), 8.35 (broad s,1 H).

A mixture of N-benzyl-N-methyl-2-(5-chloro-3-1H-indolyl)ethylamine (16 g, 0.054 mol), 4-fluoro-iodobenzene (14.3 g, 0.064 mol), K$_2$CO$_3$ (11.1 g, 0.080 mol) and 1-methyl-2-pyrrolidinone (200 mL) was heated at 165° C. for 8 h. After cooling to room temperature water (250 mL) was added and the thus formed mixture was extracted with diethyl ether (2×300 mL). The combined organic phases were washed with brine (3×500 mL) and dried (Na$_2$SO$_4$). Evaporation of the solvent afforded an oil that was purified by column chromatography (eluted with ethyl acetate/heptane 1:3) affording pure title compound as an oil: 13.7 g (26%) $^1$H NMR (CDCl$_3$) δ 2.35 (s, 3 H), 2.70–2.80 (m, 2 H), 2.90–3.00 (m, 2 H), 3.60 (s, 2 H), 7.05–7.40 (m, 12 H), 7.55 (broad s, 1 H).

The following compounds were prepared in a similar way:

N,N-Dimethyl-2-(5-chloro-1-(4-fluorophenyl)-3-1H-indolyl)ethylamine maleate (14b): mp 170°–172° C. (ethyl acetate); $^1$H NMR (CDCl$_3$) δ 2.90 (s, 6 H), 3.20–3.30 (m, 2 H), 3.30–3.45 (m, 2 H), 6.30 (s, 2 H), 7.15–7.30 (m, 4 H), 7.35 (d, 1 H), 7.40 (dd, 2 H), 7.60 (broad s, 1 H); MS (m/z) 317 (MH$^+$, 11), 272 (72), 237 (46), 236 (27). Anal. (C$_{18}$H$_{18}$ClFN$_2$.C$_4$H$_4$O$_4$) C, H, N.

5-chloro-1-(4-fluorophenyl)-3-(2-(4-morpholinyl)ethyl)-1H-indole fumarate(14c): mp 191°–193° C. (ethanol); $^1$H NMR (DMSO-d$_6$) δ 2.60–2.70 (m, 4 H), 2.75–2.85 (m, 2 H), 2.90–3.00 (m, 2 H), 3.60 (m, 4 H), 6.65 (s, 2 H), 7.20 (broad d, 1 H), 7.35–7.50 (m, 3 H), 7.55 (s, 1 H), 7.60 (dd, 2 H), 7.75 (broad s, 1 H); MS (m/z) 359 (MH$^+$, 3), 272 (77), 237 (14), 100 (100). Anal. (C$_{20}$H$_{20}$ClFN$_2$O.C$_4$H$_4$O$_4$) C, H, N.

Example 14

N-methyl-2-(5-chloro-1-(4-fluorophenyl)-3-1H-indolyl)ethylamine Maleate (15a)

A mixture of N-benzyl-N-methyl-2-[5-chloro-1-(4-fluorophenyl)-3-1H-indolyl]ethylamine (14a) (13.7 g, 0.026 mol), methyl chloroformate (2.9 g, 0.031), K$_2$CO$_3$ (4.2 g, 0.031) and 1,1,1-trichloroethane (150 mL) was heated at reflux for 2 h and the precipitates was filtered off. Evaporation of the solvents afforded crude N-methyl-N-methoxycarbonyl-2-[5-chloro-1-(4-fluorophenyl)-3-1H-indolyl]ethylamine (12.2 g) as an oil. A mixture of the crude N-methoxycarbonyl-2-[5-chloro-1-(4-fluorophenyl)-3-1H-indolyl]ethylamine (12.2 g, 0.034) and 47% hydrobromic acid (150 mL) was heated at reflux for 14 h. The reaction mixture was poured into ice, made alkaline with concentrated NaOH and extracted with diethyl ether (2×200 mL). The combined organic phases were washed with brine and dried (Na$_2$SO$_4$). Evaporation of the solvents afforded pure title compound as an oil (7.9 g, 52%) which was crystalized as its maleate from ethyl acetate: mp 171°–173° C. (ethyl acetate); $^1$H NMR (DMSO-d$_6$) δ 2.65 (s, 3 H), 3.05–3.20 (m, 2 H), 3.20–3.30 (m, 2 H), 6.05 (s, 2 H), 7.20 (broad d, 1 H), 7.45 (t, 2 H), 7.50 (s, 1 H), 7.60 (dd, 2 H), 7.65 (s, 1 H), 7.80 (broad s, 1 H); MS (m/z) 303 (MH$^+$), 237 (82) 236 (100). Anal. (C$_{17}$H$_{16}$FClN$_2$.C$_4$H$_4$O$_4$) C, H, N.

Example 15 (Method g)

N,N-Dimethyl-2-[5-bromo-1-(4-fluorophenyl)-1H-indol-3-yloxy]ethylamine, Hydrochloride (16a)

The starting material 5-bromo-1-(4-fluorophenyl)-3-hydroxy-1H-indole-2-carboxylic acid methyl ester was prepared according to literature procedures (Unangst et al. J.Heterocyc.Chem. 1984, 21, 709–714 and J.Heterocyc.Chem. 1987, 811–815.). To a solution of this methyl ester (36 g) in acetone (250 mL) was added anh. potassium carbonate (20 g). The mixture was heated to reflux temperatures and a solution of 1-chloro-N,N-dimethylacetamide (15 g) in acetone (30 ml) was added dropwise during 25 minutes. The mixture was further refluxed for 2 hours. After cooling the mixture was worked up as above leaving 45 g of the crude N,N-dimethylacetamide derivative as an visceous oil which was used without further purification. To a solution of N,N-dimethyl-1-[5-bromo-1-(4-fluorophenyl)-2-methoxycarbonylo-1H-indol-3-yloxy]acetamide (44 g) in methanol was added an aqueous solution (50 ml) of potassium hydroxide (11 g). After reflux for 2 hours the precipitated potassium salt was filtered off and subsequently dissolved in water. pH was adjusted to <1 by addition of diluted hydrochloric acid. The precipitated carboxylic acid was filtered off, washed with water and finally dried in vacuo. Yield: 36 g. Mp: 146°–150° C. To a solution of the thus isolated N,N-dimethyl-1-[5-bromo-2-carboxy-1-(4-fluorophenyl)-1H-indol-3-yloxy]acetamide (10 g) in NMP (100 mL) was added Cu powder (1 g). The mixture was heated at 185°–190° C. for 16 hours. After cooling to room temperature precipitates were filtered off and ethyl acetate, water and diluted aqueous NH$_4$OH were added (pH>10). The organic phase was separated and worked up as above leaving the crude product as an oil. Pure N,N-dimethyl-1-[5-bromo-1-(4-fluorophenyl)-1H-indol-3-yloxy]acetamide (5 g) was obtained by column chromatography. All of the thus isolated acetamide derivative was dissolved in diethyl ether and added dropwise to a suspension of lithium aluminium hydride (1 g) in diethyl ether at reflux temperature. After reflux for 3 hours the mixture was cooled to 10° C. and water (1 mL) and diluted aqueous NaOH solution (2 mL) were added cautiously. The precipitated inorganic salts were filtered off and the filter cake was washed carefully with dichloromethane (2×50 mL). The combined organic phases were dried (anh. MgSO$_4$) and the solvents were evaporated in vacuo leaving the crude title compound as an oil (3 g). The crude product was dissolved in acetone and upon addition of an ether solution of HCl, the hydrochloric salt precipitated. Yield of 16a 2 g. Recrystallisation from 2-propanol gave a pure product with mp 189°–190° C. $^1$H NMR (DMSO-d$_6$) δ 2.85 (s, 6H), 3.55 (t, 2H), 4.45 (t, 2H), 7.30 (dd, 1H), 7.35–7.45 (m, 3H), 7.55 (s, 1H), 7.60 (dd, 2H), 7.90 (d, 1H), 10.95 (s,1 H). MS (m/z) 377 (MH⁺), 72 (100). Anal. ($C_{18}H_{18}BrClFN_2 \cdot HCl$) C, H, N.

Example 16 (Method h)

N,N-Dimethyl-2-[5-cyano-1-(4-fluorophenyl)-1H-indol-3-yloxy]ethylamine, Hydrochloride (17a)

To a solution of N,N-dimethyl-2-[5-bromo-1-(4-fluorophenyl)-1H-indol-3-yloxy]ethylamine (4 g) prepared as in Example 11 in NMP (30 mL) was added CuCN (3 g). The mixture was heated at 160° C. for 9 hours. The mixture was poured into a solution of NaCN (5 g) in water (50 mL) while still hot. After stirring for 10 minutes ethyl acetate (2×50 mL) was added. The combined organic phase was worked up as above. The crude product was purified by column chromatography (eluent: ethyl acetate/ethanol/triethylamine: 90/10/4) on silica gel. Yield 1.5 g. The hydrochloric salt precipitated from acetone. Mp 221°–223° C. $^1$H NMR (DMSO-$d_6$) δ 2.85 (s, 6H), 3.55 (t, 2H), 4.45 (t, 2H), 7.45 (t, 2H), 7.55–7.70 (m, 5H), 8.30 (s,1 H), 10.85 (s, 1 H); MS (m/z) 324 (MH⁺, 2), 72 (100). Anal. ($C_{19}H_{18}ClFN_3 \cdot HCl$)) C, H, N.

Pharmacology

The compounds of Formula I have been tested in established and reliable pharmacological methods for determination of the activity at the 5-HT$_2$ receptor and the dopamine D$_2$ receptor, respectively. The tests were as descibed in the following.

Inhibition of $^3$H-Ketanserin Binding to 5-HT$_2$ Receptors in Rat Cortex in vitro By this method the inhibition by drugs of the binding of $^3$H-Ketanserin (0.5 nM) to 5-HT$_2$ receptors in membranes from rat is determined in vitro. The method is described in Hyttel, *Pharmacol. & Toxicol.* 61, 126–129, 1987. The results are shown in Table 1.

Inhibition of $^3$H-Spiroperidol Binding to Dopamine D$_2$ Receptors in Rat Corpus Striatum in vitro By this method the inhibition by drugs of the binding of $^3$H-spiroperidol (0.5 nM) to dopamine D$_2$ receptors in membranes from rat corpus striatum is determined in vitro. The method is described in Hyttel & Larsen, *J. Neurochem*, 44, 1615–1622, 1985). The results are shown in Table 1.

Quipazine Inhibition

Quipazine is a 5-HT$_2$ agonist, which induces head twitches in rats. The test is a test for 5-HT$_2$-antagonistic effect testing the ability to inhibit head twitches. The test is performed as published by Arnt et al. (*Drug Development Research*, 16, 59–70, 1989).

Antagonism of Pergolide-induced Circling Behaviour in Rats with Unilateral 6-OHDA Lesions This test, which is an extremely sensitive test for dopamine D-2 antagonism in vivo was performed as described in Arnt, J. and Hyttel J., *Eur. J. Pharmacol.* 102, 349–354, 1984; and Arnt, J. and Hyttel J, *J. Neural. Transm.* 67, 225–240, 1986.

TABLE 1

| RECEPTOR BINDING DATA ($IC_{50}$ values in nM) | | |
|---|---|---|
| Compound No. | 5-HT$_2$ binding $^3$H ketanserin | Dopamin D$_2$ binding $^3$H spiroperidol |
| 3a | 19 | 42 |
| 3b | 7.8 | 190 |

TABLE 1-continued

| RECEPTOR BINDING DATA ($IC_{50}$ values in nM) | | |
|---|---|---|
| Compound No. | 5-HT$_2$ binding $^3$H ketanserin | Dopamin D$_2$ binding $^3$H spiroperidol |
| 3c | 310 | 26 |
| 3d | 110 | 21 |
| 4a | 4.2 | 2.9 |
| 4b | 0.88 | 5.8 |
| 4c | 18 | 18 |
| 4d | 220 | 190 |
| 4e | 5.9 | 2.3 |
| 4f | 48 | 27 |
| 4h | 2.0 | 200 |
| 4i | 6.3 | 120 |
| 4j | 17 | 63 |
| 4k | 21 | 2.6 |
| 4n | 28 | 4.7 |
| 4o | 30 | 23 |
| 4p | 35 | 17 |
| 4q | 43 | 140 |
| 4r | 86 | 770 |
| 4s | 20 | 22 |
| 4u | 1.0 | 19 |
| 4v | 5.3 | 25 |
| 6a | 7.4 | 5.5 |
| 6b | 21 | 37 |
| 6c | 42 | 330 |
| 7a | 18 | 30 |
| 7b | 8.2 | 18 |
| 8a | 49 | 8.1 |
| 8b | 220 | 35 |
| 9a | 38 | 430 |
| 10 | 11 | 83 |
| 13a | 12 | 19 |
| 13b | 21 | 33 |
| 14b | 8.9 | 38 |
| 14c | 22 | 54 |
| 15a | 17 | 24 |
| 16a | 7.0 | 6.2 |
| 17a | 21 | 0.98 |

Results

It appears from Table 1 that the compounds of the invention are 5-HT$_2$ receptor ligands and many of them additionally D$_2$ receptor ligands in vitro. Furthermore, it was found in the Quipazine inhibition test that they are in general 5-HT$_2$ receptor antagonists in vivo. Furthermore, the test for inhibition of pergolide induced circling behaviour showed that many of the compounds are dopamine D$_2$ antagonists in vivo.

Formulation Examples

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine.

Examples of adjuvants or diluents comprise: corn starch, lactose, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the vehicle, preferably sterile water, adjusting the solution to the desired volume, sterilization of the solution and filling in suitable ampules or vials. Any suitable additive conventionally used in the art may be added, such as tonicity agents, preservatives, antioxidants, etc.

Typical examples of recipes for the formulations of the invention are as follows:

| 1) Tablets containing 5 milligrams of Compound 4h calculated as the free base: | |
|---|---|
| Compound 4h | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |
| 2) Tablets containing 1 milligram of Compound 4b calculated as the free base: | |
| Compound 4b | 1.0 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |
| 3) Syrup containing per milliliter: | |
| Compound 10 | 5.0 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 mL |
| Flavour | 0.05 mg |
| Saccharin natrium | 0.5 mg |
| Water | ad 1 mL |
| 4) Solution for injection containing per milliliter: | |
| Compound 3b | 0.5 mg |
| Sorbitol | 5.1 mg |
| Acetic acid | 0.08 mg |
| Water for injection | ad 1 mL |

We claim:

1. A 3-substituted 1-arylindole compound having general Formula I

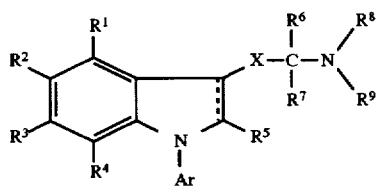

wherein Ar is selected from the group consisting of phenyl, 2-thienyl, 3-thienyl, 2-furyl, 3-furyl, 2-pyridyl, 3-pyridyl, and 4-pyridyl, wherein said Ar groups can be substituted with one or more substituents selected from the group consisting of halogen, lower alkyl, lower alkoxy, hydroxy, trifluoromethyl, and cyano;

X represents a divalent spacer selected from the group consisting of A—$CR^aR^b$ and $CR^cR^d$, wherein A is O, or $CR^eR^f$, and $R^a$ to $R^f$ are hydrogen, lower alkyl or lower alkenyl;

the dashed line designates an optional bond;

$R^1$–$R^4$ are independently selected from the group consisting of hydrogen, halogen, lower alkyl, lower alkoxy, hydroxy, nitro, lower alkylthio, lower alkylsulfonyl, lower alkylamino, lower dialkylamino, cyano, trifluoromethyl, trifluoromethylsulfonyloxy and trifluoromethylthio;

$R^5$ is hydrogen, hydroxy, lower alkoxy, halogen, trifluoromethyl, lower alkyl optionally substituted with hydroxy or lower alkenyl optionally substituted with hydroxy;

$R^8$ is lower alkyl, lower alkenyl optionally substituted with one or two hydroxy groups, or $R^8$ represents a group of Formula 1a or 1b:

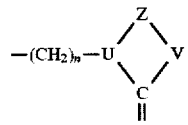

or

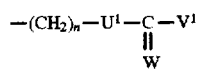

wherein n is an integer from 2–8; W is O or S; U is N or CH; Z is $(CH_2)_m$, m being 2 or 3, 1,2-phenylene optionally substituted with halogen or trifluoromethyl, CH=CH, $COCH_2$ or $CSCH_2$; V is O, S, $CH_2$ or $NR^{10}$, wherein $R^{10}$ is selected from the group consisting of hydrogen, lower alkyl, lower alkenyl, cycloalkyl, and cycloalkyl-lower alkyl, each optionally substituted with one or two hydroxy groups;

$U^1$ is O, S, $CH_2$ or a group $NR^{11}$, wherein $R^{11}$ is selected from the group consisting of hydrogen, lower alkyl, lower alkenyl, cycloalkyl, and cycloalkyl-lower alkyl, each optionally substituted with one or two hydroxy groups; and $V^1$ is $NR^{12}R^{13}$, $OR^{14}$, $SR^{15}$ or $CR^{16}R^{17}R^{18}$, where $R^{12}$–$R^{18}$ are independently selected from the group consisting of hydrogen, lower alkyl, lower alkenyl, cycloalkyl, and cycloalkyl-lower alkyl, each optionally substituted with one or two hydroxy groups;

$R^9$ is hydrogen, lower alkyl, lower alkenyl or lower alkynyl; or $R^9$ is linked to $R^7$ in order to form a 5–6 membered ring containing one nitrogen atom; or $R^8$ and $R^9$ together with the nitrogen atom to which they are attached form a group of Formula 1c

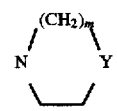

wherein m is 1 or 2, Y is O, S or a group CH—$R^{19}$ where $R^{19}$ is hydrogen, lower alkyl or lower alkenyl, optionally substituted with one or two hydroxy groups; a group of Formula 1a or 1b as defined above; or a group $CONR^{20}R^{21}$, where $R^{20}$ and $R^{21}$ are hydrogen or lower alkyl, provided that Y may not be O or S when m is 1; and pharmaceutically acceptable salts thereof; wherein when X is $CR^cR^d$, and $R^c$ and $R^d$ are both H, then $R^8$ and $R^9$ (a) are not $C_1$–$C_4$ alkyl or $C_1$–$C_4$ alkenyl either being optionally substituted with one or two hydroxy groups or (b) together with the N atom to which they are attached do not form a group of Formula 1c; and wherein when $R^8$ and $R^9$ are H or $C_1$–$C_4$ alkyl or together with the N atom to which they are attached form a group of Formula 1c, X is not A—$CR^a$ $R^b$ wherein A is $CR^eR^f$ and $R^a$, $R^b$, $R^e$ and $R^f$ are all H.

2. A compound according to claim 1, wherein Ar is phenyl or phenyl substituted with halogen.

3. A compound according to claim 2, wherein Ar is 4-fluorophenyl.

4. A compound according to claim 1, wherein X is $CR^cR^d$, O—$CR^aR^b$ or $CR^eR^f$—$CR^aR^b$.

5. A compound according to claim 4, wherein X is O—$CR^aR^b$ and $R^a$ and $R^b$ are hydrogen.

6. A compound according to claim 1, wherein the dashed line designates a bond.

7. A compound according to claim 1, wherein $R^1$ and $R^4$ are hydrogen, $R^2$ and $R^3$ are hydrogen, halogen, or cyano, $R^5$ is hydrogen, lower alkyl or lower alkyl substituted with hydroxy, and $R^6$ is hydrogen or lower alkyl.

8. A compound according to claim 1, wherein $R^7$ is hydrogen or lower alkyl, or $R^7$ is linked to $R^9$ in order to form a 5–6 membered ring.

9. A compound according to claim 1, wherein $R^8$ is lower alkyl or a group of Formula 1a wherein n is 2, 3, or 4; W is O; U is N; V is $NR^{10}$, wherein $R^{10}$ is hydrogen, lower alkyl or lower alkenyl; and $R^9$ is hydrogen, lower alkyl or lower alkenyl; or $R^9$ is linked to $R^7$ in order to form a 5- or 6-membered ring, containing one nitrogen atom.

10. A compound according to claim 1, wherein $R^8$ and $R^9$ together with the nitrogen atom to which they are attached form a group of Formula 1c wherein Y is O or a group CH—$R^{19}$ where $R^{19}$ is hydrogen, lower alkyl, a group of Formula 1a, or a group $CONR^{20}R^{21}$, where $R^{20}$ and $R^{21}$ are hydrogen or lower alkyl.

11. A compound according to claim 1, wherein X is O—$CH_2$, $CH_2$—$CH_2$ or $CH_2$; $R^1$ and $R^4$ are hydrogen; $R^2$ and $R^3$ are independently selected from the group consisting of hydrogen, halogen, lower alkyl, lower alkoxy, hydroxy, nitro, lower alkylthio, lower alkylsulfonyl, lower alkylamino, lower dialkylamino, cyano, trifluoromethyl, trifluoromethylsulfonyloxy and trifluoromethylthio;

$R^8$ is a group of Formula 1a wherein n is 2, 3, or 4; W is O; U is N; V is $NR^{10}$, wherein $R^{10}$ is hydrogen or lower alkyl; and $R^9$ is lower alkyl.

12. A compound according to claim 11, wherein X is O—$CH_2$, $CH_2$—$CH_2$ or $CH_2$; and n is 2 or 3.

13. A compound according to claim 11, wherein $R^3$ is hydrogen.

14. A compound according to claim 11, wherein $R^3$ is selected from the group consisting of halogen, lower alkyl, lower alkoxy, hydroxy, nitro, lower alkylthio, lower alkylsulfonyl, lower alkylamino, lower dialkylamino, cyano, trifluoromethyl, trifluoromethylsulfonyloxy and trifluoromethylthio.

15. A compound according to claim 4, wherein X is $CR^cR^d$, O—$CR^aR^b$, or $CR^cR^f$—$CR^aR^b$, wherein $R^a$ to $R^f$ are independently hydrogen or lower alkyl.

16. A compound according to claim 15, wherein $R^a$ to $R^f$ are hydrogen.

17. A compound according to claim 7, wherein $R^2$ and $R^3$ are hydrogen, fluorine or chlorine.

18. A compound according to claim 8, wherein $R^7$ is hydrogen or methyl.

19. A compound according to claim 9, wherein $R^9$ is linked to $R^7$ forming a 5-membered ring.

20. A compound according to claim 11, wherein $R^9$ is methyl.

21. A pharmaceutical composition wherein said composition comprises at least one compound according to claim 1 together with a suitable pharmaceutically acceptable carrier or diluent wherein the daily dose is from 0.05 to 500 mg.

22. A method for treating anxiety, aggression, depression, sleep disturbances, migraine, negative symptoms of schizophrenia, psychoses, extrapyramidal side effects induced by conventional antipsychotics, abuse of drugs and substances of abuse or Parkinson's disease comprising administering a therapeutically effective amount of a compound according to claim 1 or a pharmaceutically acceptable acid addition salt thereof to a patient in need thereof.

* * * * *

UNITED STATES PATENT AND TRADEMARK OFFICE
CERTIFICATE OF CORRECTION

PATENT NO. : 5,789,404
DATED : August 4, 1998
INVENTOR(S) : Kim ANDERSEN and Jens Kristian PERREGAARD It is certified that error appears in the above-identified patent and that said Letters Patent is hereby corrected as shown below:

Column 23, after line 67, please add:

--$R^6$ and $R^7$ are independently hydrogen, lower alkyl or lower alkenyl;--

Signed and Sealed this

Twenty-sixth Day of October, 1999

Attest:

Q. TODD DICKINSON

Attesting Officer

Acting Commissioner of Patents and Trademarks